US006727085B2

(12) United States Patent
Fanø et al.

(10) Patent No.: US 6,727,085 B2
(45) Date of Patent: Apr. 27, 2004

(54) SUBTILASE VARIANTS HAVING AN IMPROVED WASH PERFORMANCE ON EGG STAINS

(76) Inventors: Tina Sejersgård Fanø, Willemoesgade 17, 3. tv., DK-2100 København Ø (DK); Frank Mikkelsen, Bykildevej 5 st. tv., DK-2500 Valby (DK)

( * ) Notice: Subject to any disclaimer, the term of this patent is extended or adjusted under 35 U.S.C. 154(b) by 0 days.

(21) Appl. No.: 09/736,116

(22) Filed: Dec. 13, 2000

(65) Prior Publication Data

US 2003/0199077 A1 Oct. 23, 2003

Related U.S. Application Data

(63) Continuation-in-part of application No. 09/574,417, filed on May 19, 2000, which is a continuation-in-part of application No. 09/487,953, filed on Jan. 19, 2000, now abandoned.
(60) Provisional application No. 60/241,207, filed on Oct. 17, 2000.

(30) Foreign Application Priority Data

| Dec. 15, 1999 | (DK) | 1999 01792 |
| May 1, 2000 | (DK) | 2000 00708 |
| Oct. 13, 2000 | (DK) | 2000 01527 |

(51) Int. Cl.$^7$ ............ C12N 9/54; C12N 15/57; C12N 15/74; C11D 3/386
(52) U.S. Cl. .......... 435/220; 435/69.1; 435/221; 435/222; 435/252.3; 435/320.1; 435/471; 536/23.2; 510/392
(58) Field of Search ............. 435/69.1, 220, 435/221, 222, 471, 264, 252.3, 320.1; 510/392; 536/23.2

(56) References Cited

U.S. PATENT DOCUMENTS 4,760,025 A * 7/1988 Estell et al. ............ 510/392
4,914,031 A * 4/1990 Zukowski et al. ......... 435/222

(List continued on next page.)

FOREIGN PATENT DOCUMENTS

| EP | 0 130 756 | 1/1985 |
| EP | 214 435 | 3/1987 |
| EP | 0 251 446 | 1/1988 |
| EP | 0 260 105 | 3/1988 |
| EP | 0 357 157 A1 * | 3/1990 |
| EP | 0 525 610 A2 | 2/1993 |

(List continued on next page.)

OTHER PUBLICATIONS

Thomas, P. G., et al., 1985, "Tailoring the pH dependence of enzyme catalysis using protein engineering", Nature, vol. 318, pp. 375–376.*
Estell et al., 1986, "Probing steric and hydrophobic effects on enzyme–substrate interactions by protein interactions by protein engineering", Science, vol. 233, pp. 659–663.*
Wells et al., 1987, "Designing substrate specificity by protein engineering of electrostatic interactions", Proceedings of the National Academy of Sciences, U.S.A., vol. 84, pp. 1219–1223.*

(List continued on next page.)

Primary Examiner—Nashaat T. Nashed
Assistant Examiner—William W. Moore
(74) Attorney, Agent, or Firm—Elias J. Lambiris

(57) ABSTRACT

The present invention relates to the use of a subtilase variant for removal of egg stains from laundry or from hard surfaces, where the subtilase variant comprises at least one additional amino acid residue in the active site loop (b) region from position 95 to 103 (BASBPN numbering). These subtilase variants are useful exhibiting excellent or improved wash performance on egg stains when used in e.g. cleaning or detergent compositions, including automatic dishwash compositions. The present invention also relates to novel subtilase variants, to isolated DNA sequences encoding the variants, expression vectors, host cells, and methods for producing and using the variants of the invention. Further, the present invention relates to cleaning and detergent compositions comprising the variants of the invention.

30 Claims, 1 Drawing Sheet

```
No:      1       10        20        30        40        50
a)  AQSVPYGVSQIKAPALHSQGYTGSNVKVAVIDSGIDSSHPDLKVAGGASM
b)  AQSVPWGISRVQAPAAHNRGLTGSGVKVAVLDTGI*STHPDLNIRGGASF

No:             60        70        80        90       100
a)  VPSETNPFQDNNSHGTHVAGTVAALNNSIGVLGVAPSASLYAVKVLGADG
b)  VPGEPST*QDGNGHGTHVAGTVAALNNSIGVIGVAPSADLYAVKVLGANG

No:            110       120       130       140       150
a)  SGQYSWIINGIEWAIANNMDVINMSLGGPSGSAALKAAVDKAVASGVVVV
b)  RGSVSGIAQGLEWAAANKMHIANMELGSDAPSTTLERAVNYATSQGVLVI

No:            160       170       180       190       200
a)  AAAGNEGTSGSSSTVGYPGKYPSVIAVGAVDSSNQRASFSSVGPELDVMA
b)  AATGNNG*SGS***VGYPARYANAMAVGATDQNNRRANFSQYGTGIDIVA

No:            210       220       230       240       250
a)  PGVSIQSTLPGNKYGAYNGTSMASPHVAGAAALILSKHPNWTNTQVRSSL
b)  PGVDIEGTYPGSSYDSLSGTSMATPHVAGVAALVKQKNPSWSNVQIRNHL

No:            260       270  275
a)  ENTTTKLGDSFYYGKGLINVQAAAQ
b)  KNTATSLGSTNLYGSGLVNAEAATR
```

U.S. PATENT DOCUMENTS

| | | | |
|---|---|---|---|
| 4,980,288 A | * | 12/1990 | Bryan et al. ............... 435/222 |
| 4,990,452 A | * | 2/1991 | Bryan et al. ............... 435/222 |
| 5,013,657 A | * | 5/1991 | Bryan et al. ............... 435/222 |
| 5,116,741 A | * | 5/1992 | Bryan et al. ................ 435/87 |
| 5,118,623 A | * | 6/1992 | Boguslawski et al. ...... 510/374 |
| 5,208,158 A | * | 5/1993 | Bech et al. ............... 435/219 |
| 5,260,207 A | * | 11/1993 | Pantoliano et al. ......... 435/221 |
| RE34,606 E | | 5/1994 | Estell et al. ............... 510/392 |
| 5,336,611 A | * | 8/1994 | van Eekelen et al. ....... 435/221 |
| 5,397,705 A | * | 3/1995 | Zukowski et al. .......... 435/222 |
| 5,399,283 A | * | 3/1995 | Stabinsky et al. .......... 510/392 |
| 5,482,849 A | * | 1/1996 | Branner et al. ............ 435/222 |
| 5,543,302 A | | 8/1996 | Boguslawski et al. ..... 435/69.1 |
| 5,631,217 A | * | 5/1997 | Branner et al. ............ 510/320 |
| 5,665,587 A | * | 9/1997 | Aaslyng et al. ............ 435/221 |
| 5,677,272 A | * | 10/1997 | Ghosh et al. ............... 510/306 |
| 5,700,676 A | * | 12/1997 | Bott et al. .................. 435/221 |
| 5,741,694 A | * | 4/1998 | Hastrup et al. ............. 435/222 |
| 5,837,517 A | * | 11/1998 | Sierkstra et al. ........... 435/221 |
| 6,190,900 B1 | * | 2/2001 | Sierkstra et al. ........... 435/221 |
| 6,197,567 B1 | * | 3/2001 | Aaslyng et al. ............ 435/221 |
| 6,300,116 B1 | * | 10/2001 | von der Osten et al. .... 435/220 |

FOREIGN PATENT DOCUMENTS

| | | |
|---|---|---|
| WO | WO 87/04461 | 7/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95/27049 | 10/1995 |
| WO | WO 95/29979 | 11/1995 |
| WO | WO 95/30010 | 11/1995 |
| WO | WO 95/30011 | 11/1995 |
| WO | WO 87/05050 | 8/1997 |
| WO | WO 00/37599 | 6/2000 |
| WO | WO 00/37621 | 6/2000 |
| WO | WO 00/37658 | 6/2000 |

OTHER PUBLICATIONS

Russell et al., 1987, "Rational modification of enzyme catalysis by engineering surface charge", Nature, vol. 328, pp. 496–500.*

Cunningham et al., 1987, "Improvement in the alkaline stability of subtilisin using an efficient random mutagenesis and screening procedure", Protein Engineering, vol. 1, pp. 319–325.*

Sternberg et al., 1987, "Prediction of electrostatic effects of engineering of protein charges", Nature, vol. 330, pp. 86–88.*

Siezen, R. J. et al., 1991, "Homology modelling and protein engineering strategy of subtilases, the family of subtilisin–like serine proteases", Protein Engineering, vol. 4, No. 7, pp, 719–737.*

Koide et al., 1986, "Cloning and sequencing of the major intracellular serine protease gene of *Bacillus subtilis*", Journal of Bacteriology, vol. 167, pp. 110–116.*

Russell et al., Nature, vol. 328, pp. 496–500 (1987).

Thomas et al., Nature, vol. 318, pp. 375–376 (1985).

Russell et al., J. Mol. Biol., vol. 193, pp. 803–813 (1987).

* cited by examiner

| No: | 1 | 10 | 20 | 30 | 40 | 50 |
|---|---|---|---|---|---|---|
| a) | AQSVPYGVSQIKAPALHSQGYTGSNVKVAVIDSGIDSSHPDLKVAGGASM |||||||
| b) | AQSVPWGISRVQAPAAHNRGLTGSGVKVAVLDTGI*STHPDLNIRGGASF |||||||

| No: | | 60 | 70 | 80 | 90 | 100 |
|---|---|---|---|---|---|---|
| a) | VPSETNPFQDNNSHGTHVAGTVAALNNSIGVLGVAPSASLYAVKVLGADG ||||||
| b) | VPGEPST*QDGNGHGTHVAGTVAALNNSIGVIGVAPSADLYAVKVLGANG ||||||

| No: | | 110 | 120 | 130 | 140 | 150 |
|---|---|---|---|---|---|---|
| a) | SGQYSWIINGIEWAIANNMDVINMSLGGPSGSAALKAAVDKAVASGVVVV ||||||
| b) | RGSVSGIAQGLEWAAANNMHIANMSLGSDAPSTTLERAVNYATSQGVLVI ||||||

| No: | | 160 | 170 | 180 | 190 | 200 |
|---|---|---|---|---|---|---|
| a) | AAAGNEGTSGSSSTVGYPGKYPSVIAVGAVDSSNQRASFSSVGPELDVMA ||||||
| b) | AATGNNG*SGS***VGYPARYANAMAVGATDQNNRRANFSQYGTGIDIVA ||||||

| No: | | 210 | 220 | 230 | 240 | 250 |
|---|---|---|---|---|---|---|
| a) | PGVSIQSTLPGNKYGAYNGTSMASPHVAGAAALILSKHPNWTNTQVRSSL ||||||
| b) | PGVDIESTYPGSSYDSLSGTSMATPHVAGVAALVKQKNPSWSNVQIRNHL ||||||

| No: | | 260 | 270 | 275 | | |
|---|---|---|---|---|---|---|
| a) | ENTTTKLGDSFYYGKGLINVQAAAQ ||||||
| b) | KNTATSLGSTNLYGSGLVNAEAATR ||||||

Fig. 1

SUBTILASE VARIANTS HAVING AN IMPROVED WASH PERFORMANCE ON EGG STAINS

CROSS-REFERENCE TO RELATED APPLICATIONS

This application is a continuation-in-part of U.S. Ser. No. 09/574,417, filed May 19, 2000, which is a continuation-in-part of U.S. Ser. No. 09/487,953 filed on Jan. 19, 2000, now abandoned and claims priority under 35 U.S.C. 119 of Danish application nos. PA 1999 01792 filed on Dec. 15, 1999 and PA 2000 15207 filed on Oct. 13, 2000, and U.S. provisional application No. 60/241,207 filed on Oct. 17, 2000, the contents of which are fully incorporated herein by reference.

TECHNICAL FIELD

The present invention relates to the use of subtilase variants for removal of egg stains from laundry or from hard surfaces. In particular the present invention relates to the use of a subtilase variant for removal of egg stains from laundry or from hard surfaces, where the subtilase variant comprises at least one additional amino acid residue in the active site loop (b) region from position 95 to 103 (BASBPN numbering, vide infra). These subtilase variants are useful exhibiting excellent or improved wash performance on egg stains when used in e.g. cleaning or detergent compositions, such as laundry detergent compositions and dishwash composition, including automatic dishwash compositions. The present invention also relates to novel subtilase variants, to isolated DNA sequences encoding the variants, expression vectors, host cells, and methods for producing and using the variants of the invention. Further, the present invention relates to cleaning and detergent compositions comprising the variants of the invention.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novo Nordisk A/S), RELASE® (Novo Nordisk A/S), MAXAPEM® (Gist-Brocades N.V.), PURAFECT® (Genencor International, Inc.).

Further, a number of protease variants are described in the art. A thorough list of prior art protease variants is given in WO 99/27082.

However, even though a number of useful protease variants have been described, there is still a need for new improved proteases or protease variants for a number of industrial uses.

In particular, the problem of removing egg stains from e.g. laundry or hard surfaces has been pronounced due to the fact that many proteases are inhibited by substances present in the egg white. Examples of such substances include trypsin inhibitor type IV-0 (Ovo-inhibitor) and trypsin inhibitor type III-0 (Ovomucoid).

Therefore, an object of the present invention, is to provide improved subtilase variants, which are not, or which are only to a limited extent, inhibited by such substances. A further object of the present invention is to provide improved subtilase variants, which are suitable for removal of egg stains from, for example, laundry and/or hard surfaces.

SUMMARY OF THE INVENTION

Thus, in a first aspect the present invention relates to the use of a subtilase variant for removal of egg stains from laundry or from hard surfaces, the subtilase variant comprising at least one additional amino acid residue in the active site loop (b) region from position 95 to 103 (BASBPN numbering).

In a second aspect the present invention relates to a subtilase variant selected from the group consisting of a variant comprising at least one additional amino acid residue in the active site (b) loop corresponding to the insertion of at least one additional amino acid residue between positions 98 and 99 and further comprising at least one additional modification (BASBPN numbering), and a variant comprising at least one additional amino acid residue in the active site (b) loop corresponding to the insertion of at least one additional amino acid residue between positions 99 and 100 and further comprising at least one additional modification (BASBPN numbering), where the variant—when tested in the "Ovo-inhibition Assay" disclosed in Example 4 herein—has a Residual Activity of at least 10%.

In a third aspect the present invention relates to a subtilase variant selected from the group consisting of a variant comprising an insertion of at least one additional amino acid residue between positions 98 and 99 and further comprising a substitution in positions 133 and 143, a variant comprising an insertion of at least one additional amino acid residue between positions 99 and 100 and further comprising a substitution in position 99, a variant comprising an insertion of at least one additional amino acid residue between positions 98 and 99 and further comprising substitutions in positions 167, 170 and 194, a variant comprising an insertion of at least one additional amino acid residue between positions 99 and 100 and further comprising an insertion of at least one additional amino acid residue between positions 216 and 217, a variant comprising an insertion of at least one additional amino acid residue between positions 99 and 100 and further comprising an insertion of at least one additional amino acid residue between positions 217 and 218, a variant comprising an insertion of at least one additional amino acid residue between positions 99 and 100 and further comprising an insertion of at least one additional amino acid residue between positions 42 and 43, and a variant comprising an insertion of at least one additional amino acid residue between positions 99 and 100 and further comprising an insertion of at least one additional amino acid residue between positions 129 and 130.

In a fourth aspect the present invention relates to an isolated DNA sequence encoding a subtilase variant of the invention.

In a fifth aspect the present invention relates to an expression vector comprising the isolated DNA sequence of the invention.

In a sixth aspect the present invention relates to a microbial host cell transformed with the expression vector of the invention.

In a seventh aspect the present invention relates to a method for producing a subtilase variant according to the invention, wherein a host according to the invention is cultured under conditions conducive to the expression and secretion of said variant, and the variant is recovered.

In an eight aspect the present invention relates to a cleaning or detergent composition, preferably a laundry or dishwash composition, comprising the variant of the invention.

In a ninth aspect the present invention relates to a method for removal of egg stains from a hard surface or from laundry, the method comprising contacting the egg stain-containing hard surface or the egg stain-containing laundry with a cleaning or detergent composition, preferably a laundry or dishwash composition, containing a subtilase variant comprising at least one additional amino acid residue in the active site loop (b) region from position 95 to 103 (BASBPN numbering).

Still other aspect of the present invention will be apparent from the below description and from the appended claims.

Concerning alignment and numbering reference is made to FIG. 1 which shows an alignments between subtilisin BPN' (a) (BASBPN) and subtilisin 309 (BLSAVI) (b).

These alignments are in this patent application used as a reference for numbering the residues.

Definitions

Prior to discussing this invention in further detail, the following terms and conventions will first be defined.

Nomenclature and Conventions for Designation of Variants

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Thereby a number of deletions and insertions will be defined in relation to BASBPN. In FIG. 1, subtilisin 309 (Savinase®) has 6 deletions in positions 36, 58, 158, 162, 163, and 164 in comparison to BASBPN. These deletions are in FIG. 1 indicated by asterixes (*).

The various modifications performed in a parent enzyme is indicated in general using three elements as follows:

Original Amino Acid Position Substituted Amino Acid

The notation G195E thus means a substitution of a glycine in position 195 with a glutamic acid.

In the case where the original amino acid residue may be any amino acid residue, a short hand notation may at times be used indicating only the position and substituted amino acid:

Position Substituted Amino Acid

Such a notation is particular relevant in connection with modification(s) in homologous subtilases (vide infra).

Similarly when the identity of the substituting amino acid residue(s) is immaterial:

Original Amino Acid Position

When both the original amino acid(s) and substituted amino acid(s) may comprise any amino acid, then only the position is indicated, e.g.: 170.

When the original amino acid(s) and/or substituted amino acid(s) may comprise more than one, but not all amino acid(s), then the selected amino acids are indicated inside brackets:

Original Amino Acid Position {Substituted Amino Acid$_1$, . . . , Substituted Amino Acid$_n$}

For specific variants the specific three or one letter codes are used, including the codes Xaa and X to indicate any amino acid residue.

Substitutions

The substitution of glutamic acid for glycine in position 195 is designated as:

Gly195Glu or G195E or the substitution of any amino acid residue acid for glycine in position 195 is designated as:

Gly195Xaa or G195X or

Gly195 or G195

The substitution of serine for any amino acid residue in position 170 would thus be designated Xaa170Ser or X170S.

or

170Ser or 170S

Such a notation is particular relevant in connection with modification(s) in homologous subtilases (vide infra). 170Ser is thus meant to comprise e.g. both a Lys170Ser modification in BASBPN and Arg170Ser modification in BLSAVI (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

Deletions

A deletion of glycine in position 195 will be indicated by:

Gly195* or G195*

Correspondingly the deletion of more than one amino acid residue, such as the deletion of glycine and leucine in positions 195 and 196 will be designated Gly195*+Leu196* or G195*+L196*

Insertions

The insertion of an additional amino acid residue such as e.g. a lysine after G195 is indicated by:

Gly195GlyLys or G195GK;

or, when more than one amino acid residue is inserted, such as e.g. a Lys, Ala and Ser after G195 this will be indicated as:

Gly195GlyLysAlaSer or G195GKAS (SEQ ID NO:1)

In such cases the inserted amino acid residue(s) are numbered by the addition of lower case letters to the position number of the amino acid residue preceding the inserted amino acid residue(s). In the above example the sequences 194 to 196 would thus be:

```
                                   (SEQ ID NO:16)
              194   195   196
    BLSAVI    A  -  G  -  L 194   195   195a  195b  195c  196
    Variant   A  -  G  -  K  -  A  -  S  -  L
```

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

```
                                   (SEQ ID NO:27)
              194   195   196
    BLSAVI    A  -  G  -  L to 194   195   195a  196
    Variant   A  -  G  -  G  -  L
              194   194a  195   196
```

Such instances will be apparent to the skilled person, and the indication G195GG and corresponding indications for this type of insertions are thus meant to comprise such equivalent degenerate indications.

Filling a Gap

Where a deletion in an enzyme exists in the reference comparison with the subtilisin BPN' sequence used for the numbering, an insertion in such a position is indicated as:

*36Asp or *36D for the insertion of an aspartic acid in position 36

Multiple Modifications

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

Tyr167Gly+Arg170Gly,
        Tyr167Gly+Arg170Ala,

Tyr167Gly+Arg170Ser,
        Tyr167Gly+Arg170Thr,

Tyr167Ala+Arg170Gly,
        Tyr167Ala+Arg170Ala,

Tyr167Ala+Arg170Ser,
        Tyr167Ala+Arg170Thr,

Tyr167Ser+Arg170Gly,
        Tyr167Ser+Arg170Ala,

Tyr167Ser+Arg170Ser,
        Tyr167Ser+Arg170Thr,

Tyr167Thr+Arg170Gly,
        Tyr167Thr+Arg170Ala,

Tyr167Thr+Arg170Ser, and
        Tyr167Thr+Arg170Thr,

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms*. W. H. Freeman and Company, San Francisco, Chapter 3).

Numbering of Amino Acid Positions/residues

If nothing else is mentioned the amino acid numbering used herein correspond to that of the subtilase BPN' (BASBPN) sequence. For further description of the BPN' sequence, see FIG. 1 or Siezen et al., *Protein Engng.* 4 (1991) 719–737.

Serine Proteases

A serine protease is an enzyme which catalyzes the hydrolysis of peptide bonds, and in which there is an essential serine residue at the active site (White, Handler and Smith, 1973 "*Principles of Biochemistry*," Fifth Edition, McGraw-Hill Book Company, NY, pp. 271–272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711–753).

Subtilases

A sub-group of the serine proteases tentatively designated subtilases has been proposed by Siezen et al., *Protein Engng.* 4 (1991) 719–737 and Siezen et al. *Protein Science* 6 (1997) 501–523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN' (SEQ ID NO:38), subtilisin Carlsberg (ALCALASE®, NOVO NORDISK A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Gist-Brocades NV), subtilisin 309 (SEQ ID NO:49) (SAVINASE®, NOVO NORDISK A/S), subtilisin 147 (BLS147) (ESPERASE®, NOVO NORDISK A/S), and alkaline elastase YaB (BSEYAB).

Savinase®

SAVINASE® is marketed by NOVO NORDISK A/S. It is subtilisin 309 from *B. Lentus* and differs from BAALKP only in one position (N87S, see FIG. 1 herein). SAVINASE® has the amino acid sequence designated b) in FIG. 1 and as shown in SEQ ID NO:49.

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., Nature Biotechnology, 17, 893–896 (1999). Alternatively the term "parent subtilase" may be termed "wild type subtilase".

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

Specific active site loop regions, and amino acid insertions in said loops of subtilisin 309 are identified for modification herein to obtain a subtilase variant of the invention.

However, the invention is not limited to modifications of this particular subtilase, but extend to other parent (wild-type) subtilases, which have a homologous primary structure to that of subtilisin 309. The homology between two amino acid sequences is in this context described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Isolated DNA Sequence

The term "isolated", when applied to a DNA sequence molecule, denotes that the DNA sequence has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). The term "an isolated DNA sequence" may alternatively be termed "a cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained from

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove egg stains present on the object to be cleaned during e.g. wash or hard surface cleaning. See also the "Model Detergent Wash Performance Test" in Example 3 herein.

Performance Factor

The term "Performance Factor" is defined with respect to the below formula $$P = R_{variant} - R_{parent}$$

wherein P is the Performance Factor, $R_{variant}$ is the reflectance (measured at 460 nm) of the test material after being treated with a subtilase variant as described in the "Model Detergent Wash Performance Test", and $R_{parent}$ is the reflectance (measured at 460 nm) of the test material after being treated with the corresponding parent subtilase as described in the "Model Detergent Wash Performance Test". For further details, see the "Model Detergent Wash Performance Test" in Example 3 herein.

Residual Activity

The term "Residual Activity" is defined as described in the "Ovo-inhibition Assay" herein (see Example 4).

BRIEF DESCRIPTION OF THE DRAWING

FIG. 1 shows an alignment between subtilisin BPN' (a) (SEQ ID NO:38) and Savinase® (b) (SEQ ID NO:49) using the GAP routine mentioned above.

DETAILED DESCRIPTION OF THE INVENTION

The present inventors have found that subtilisin variants, wherein the active site loop (b) region is longer than those presently known, exhibit improved wash performance with respect to removal of egg stains. The identification thereof was done in constructing subtilisin variants, especially of the subtilisin 309 (BLSAVI or Savinase®), exhibiting improved wash performance properties (with respect to removal of egg stains) in model detergent compositions relative to the parent wild type enzyme.

Without being limited to any specific theory it is presently believed that the improved effect is due to an impeded binding of the egg white inhibitor in the active site loop (b) region of the subtilase variant. This in turn is probably due to structural changes of the active site loop (b) region because of insertion of one or more additional amino acid residues in this particular site of the enzyme.

Thus, variants which are contemplated as being suitable for the uses described herein are such variants where, when compared to the wild-type subtilase, one or more amino acid residues has been inserted in one or more of the following positions: between positions 95 and 96, between positions 96 and 97, between positions 97 and 98, between positions 98 and 99, between positions 99 and 100, between positions 100 and 101, between positions 101 and 102, between positions 102 and 103, between positions 103 and 104, and combinations thereof.

Preferably, the insertion is made between position 97 and 98, between positions 98 and 99, between positions 99 and 100 and/or between positions 100 and 101, in particular between positions 98 and 99 and between positions 99 and 100.

A subtilase variant of the first aspect of the invention may be a parent or wild-type subtilase identified and isolated from nature.

Such a parent wildtype subtilase may be specifically screened for by standard techniques known in the art.

One preferred way of doing this may be by specifically PCR amplify DNA regions known to encode active site loops in subtilases from numerous different microorganism, preferably different Bacillus strains.

Subtilases are a group of conserved enzymes, in the sense that their DNA and amino acid sequences are homologous. Accordingly it is possible to construct relatively specific primers flanking active site loops.

One way of doing this is by investigating an alignment of different subtilases (see e.g. Siezen et al. *Protein Science* 6 (1997) 501–523). It is from this routine work for a person skilled in the art to construct PCR primers flanking the active site loop corresponding to the active site loop (b) between amino acid residue 95 to 103 in any of the group I-S1 or I-S2 groups, such as from BLSAVI. Using such PCR primers to amplify DNA from a number of different microorganism, preferably different Bacillus strains, followed by DNA sequencing of said amplified PCR fragments, it will be possible to identify strains which produce subtilases of these groups comprising a longer, as compared to e.g. BLSAVI, active site region corresponding to the active site loop region from positions 95 to 103. Having identified the strain and a partial DNA sequence of such a subtilase of interest, it is routine work for a person skilled in the art to complete cloning, expression and purification of such a subtilase.

However, it is envisaged that a subtilase variant of the invention predominantly is a variant of a parent subtilase.

A subtilase variant suitable for the uses described herein, may be constructed by standard techniques known in the art such as by site-directed/random mutagenesis or by DNA shuffling of different subtilase sequences. See the "Material and Methods" section herein (vide infra) for further details.

As will be acknowledged by the skilled person, the variants described herein may, in addition to the at least one insertion from position 95 to 103, comprise at least one further modification. For example, the variants may comprise one or more substitutions in the active site loop (b) region as well as one or more substitutions outside said region. Furthermore, the variants may comprise one or more further insertions outside the active site loop (b) region.

Moreover, the insertions in the regions described herein may encompass insertion of more than just one amino acid residue. For example the variant according to the invention may contain one insertion, two insertions, or more than two insertions, such as three, four or five insertions.

In preferred embodiments of the present invention, the further modification is performed in a position selected from the group consisting of: substitution in position 99, substitution in position 133, substitution in position 143, substitution in position 167, substitution in position 170, substitution in position 194, insertion between positions 42 and 43, insertion between positions 129 and 130, insertion between positions 216 and 217, insertion between 217 and 218, and combinations thereof.

In an interesting embodiment of the invention the additional amino acid residue is inserted between position 98 and 99 (BASBPN numbering).

The insertion between position 98 and 99 is preferably selected from the group consisting of (in BASBPN numbering)

X98X{A,T,G, S}, e.g., X98XA,X98XT,X98XG,X98XS;
X98X{D,E,K,R}, e.g., X98XD,X98XE,X98XK,X98XR;
X98X{H,V,C,N,Q}, e.g., X98XH,X98XV,X98XC,X98XN, X98XQ; and
X98X{F,I,L,M,P,W,Y}, e.g., X98XF,X98XI,X98XL, X98XM,X98XP,X98XW,
X98XY; preferably X98XA, X98XT, X98XG or X98XS;

or more specific for subtilisin 309 and closely related subtilases, such as BAALKP, BLSUBL, and BSKSMK:

A98A{A,T,G,S}, e.g., A98AA,A98AT,A98AG,A98AS;
A98A{D,E,K,R}, e.g., A98AD,A98AE,A98AK,A98AR;
A98A{H,V,C,N,Q}, e.g., A98AH,A98AV,A98AC,A98AN, A98AQ;
A98A{F,I,L,M,P,W,Y}, e.g.,A98AF,A98AI,A98AL, A98AM,A98AP,A98AW,
A98AY; preferably A98AA, A98AT, A98AG or A98AS.

Furthermore, it is presently preferred that the insertion between position 98 and 99 is combined with a further modification, namely substitution of an amino acid residue in the positions 133 and 143, as well as substitution of an amino acid residue in the positions 167, 170 and 194.

The substitutions (in addition to the insertion between position 98 and 99) in positions 133 and 134, respectively, are preferably selected from the group consisting of X133{A,T,G,S}, e.g., X133A,X133T,X133G,X133S;
X133{D,E,K,R}, e.g., X133D,X133E,X133K,X133R;
X133{H,V,C,N,Q}, e.g., X133H,X133V,X133C,X133N, X133Q;
X133{F,I,L,M,P,W,Y}, e.g., X133F,X133I,X133L,X133M, X133P,X133W, X133Y;
X143{A,T,G,S}, e.g., X143A,X143T,X143G,X143S;
X143{D,E,K,R}, e.g., X143D,X143E,X143K,X143R;
X143{H,V,C,N,Q}, e.g., X143H,X143V,X143C,X143N, X143Q; and X143{F,I,L,M,P,W,Y}, e.g., X143F,X143I,X143L,X143M, X143P,X143W, X143Y.

In a preferred embodiment the substitution in position 133 is selected from the group consisting of X133{D,E,K,R}, preferably X133D or X133E, in particular X133E.

In another preferred embodiment the substitution in position 143 is selected from the group consisting of X143{D, E,K,R}, preferably X143K or X143R, in particular X143K.

An example of a preferred variant is a subtilase variant comprising the following insertions and substitutions: X98XS+X133E+X143K. A particular preferred variant is a subtilisin 309 variant comprising the following insertions and substitutions: A98AS+A133E+T143K.

Moreover, the substitutions (in addition to the insertion between position 98 and 99) in positions 167, 170 and 134, respectively, are preferably selected from the group consisting of X167{A,T,G,S}, e.g., X167A,X167T,X167G,X167S;
X167{D,E,K,R}, e.g., X167D,X167E,X167K,X167R;
X167{H,V,C,N,Q}, e.g., X167H,X167V,X167C,X167N, X167Q;
X167{F,I,L,M,P,W,Y}, e.g., X167F,X167I,X167L,X167M, X167P,X167W, X167Y;
X170{A,T,G,S}, e.g., X170A,X170T,X170G,X170S;
X170{D,E,K,R}, e.g., X170D,X170E,X170K,X170R;
X170{H,V,C,N,Q}, e.g., X170H,X170V,X170C,X170N, X170Q;
X170{F,I,L,M,P,W,Y}, e.g., X170F,X170I,X170L,X170M, X170P,X170W, X170Y;
X194{A,T,G,S}, e.g., X194A,X194T,X194G,X194S;
X194{D,E,K,R}, e.g., X194D,X194E,X194K,X194R;
X194{H,V,C,N,Q}, e.g., X194H,X194V,X194C,X194N, X194Q; and
X194{F,I,L,M,P,W,Y}, e.g., X194F,X194I,X194L,X194M, X194P,X194W, X194Y.

In a preferred embodiment the substitution in position 167 is selected from the group consisting of X167{A,T,G,S}, in particular X167A; the substitution in position 170 is selected from the group consisting of X170{A,T,G,S}, in particular X170S; and the substitution in position 194 is selected from the group consisting of X194{F,I,L,M,P,W,Y}, in particular X194P.

An example of a preferred variant is a subtilase variant comprising the following insertions and substitutions: X98XT+X167A+X170S+X194P. A particular preferred variant is a subtilisin 309 variant comprising the following insertions and substitutions: A98AT+Y167A+R170S+ A194P.

In a further interesting embodiment of the invention the additional amino acid residue is inserted between position 99 and 100 (BASBPN numbering).

The insertion between position 99 and 100 is preferably selected from the group consisting of (in BASBPN numbering)

X99X{A,T,G,S}, e.g., X99XA,X99XT,X99XG,X99XS;
X99X{D,E,K,R}, e.g., X99XD,X99XE,X99XK,X99XR;
X99X{H,V,C,N,Q}, e.g., X99XH,X99XV,X99XC,X99XN, X99XQ; and
X99X{F,I,L,M,P,W,Y}, e.g., X99XF,X99XI,X99XL, X99XM,X99XP,X99XW, X99XY; preferably X99X{D, E,K,R}, in particular X99XD or X99XE;

or more specific for subtilisin 309 and closely related subtilases, such as BAALKP, BLSUBL, and BSKSMK:

S99S{A,T,G,S}, e.g., S99SA,S99ST,S99SG,S99SS;
S99S{D,E,K,R}, e.g., S99SD,S99SE,S99SK,S99SR;
S99S{H,V,C,N,Q}, e.g., S99SH,S99SV,S99SC,S99SN, S99SQ;
S99S{F,I,L,M,P,W,Y}, e.g.,S99SF,S99SI,S99SL,S99SM, S99SP,S99SW, S99SY; preferably S99S{D,E,K,R}, in particular S99SD or S99SE.

With respect to insertions between position 99 and 100, it is—in one interesting embodiment of the present invention—preferred that the insertion is combined with a substitution in position 99. Thus, in addition to the contemplated insertions mentioned above, the following substitutions in position 99 are considered relevant:

X99{A,T,G,S}, e.g., X99A,X99T,X99G,X99S;
X99{D,E,K,R}, e.g., X99D,X99E,X99K,X99R;
X99{H,V,C,N,Q}, e.g., X99H,X99V,X99C,X99N,X99Q; and
X99{F,I,L,M,P,W,Y}, e.g., X99F,X99I,X99L,X99M,X99P, X99W,X99Y.

In a preferred embodiment the substitution in position 99 is selected from the group consisting of X99{A,T,G,S}, in particular X99A or X99T.

An example of a preferred variant is a subtilase variant comprising the following insertions and substitutions: X99XD+X99A or X99XR+X99T. A particular preferred variant is a subtilisin 309 variant comprising the following insertions and substitutions: S99SD+S99A or S99SR+S99T.

With respect to insertions between position 99 and 100, it is—in another interesting embodiment of the present invention—preferred that the insertion is combined with a further insertion of at least one amino acid residue between positions 216 and 217. Thus, in addition to the contemplated insertions mentioned above, the following insertions between positions 216 and 217 are considered relevant:

X216X{A,T,G,S}, e.g., X216XA,X216XT,X216XG, X216XS;
X216X{D,E,K,R}, e.g., X216XD,X216XE,X216XK, X216XR;
X216X{H,V,C,N,Q}, e.g., X216XH,X216XV,X216XC, X216XN,X216XQ; and
X216X{F,I,L,M,P,W,Y}, e.g., X216XF,X216XI,X216XL, X216XM,X216XP, X216XW,X216XY.

In a preferred embodiment the insertion between positions 216 and 217 is selected from the group consisting of X216X{F,I,L,M, P,W,Y} in particular X216XP.

Examples of preferred variants are subtilase variants comprising the following insertions and substitutions: X99XD+X99A+X216XP as well as X99XD+X99A+ X216XDP. Particular preferred variants are subtilisin 309 variants comprising the following insertions and substitutions: S99SD+S99A+S216SP as well as S99SD+S99A+ S216SDP.

With respect to insertions between position 99 and 100, it is—in still another interesting embodiment of the present invention—preferred that the insertion is combined with a further insertion of at least one amino acid residue between positions 217 and 218. Thus, in addition to the contemplated insertions mentioned above, the following insertions between positions 217 and 218 are considered relevant:

X217X{A,T,G,S}, e.g., X217XA,X217XT,X217XG, X217XS;
X217X{D,E,K,R}, e.g., X217XD,X217XE,X217XK, X217XR;
X217X{H,V,C,N,Q}, e.g., X217XH,X217XV,X217XC, X217XN,X217XQ; and
X217X{F,I,L,M,P,W,Y}, e.g., X217XF,X217XI,X217XL, X217XM,X217XP, X217XW,X217XY.

In a preferred embodiment the insertion between positions 217 and 218 is selected from the group consisting of X217X{F,I,L,M, P,W,Y} in particular X217XP.

Examples of preferred variants are subtilase variants comprising the following insertions and substitutions: X99XD+X99A+X217XP as well as X99XD+X217XP. Particular preferred variants are subtilisin 309 variants comprising the following insertions and substitutions: S99SD+ S99A+L217LP as well as S99SD+L217P.

With respect to insertions between position 99 and 100, it is—in a further interesting embodiment of the present invention—preferred that the insertion is combined with a further insertion of at least one amino acid residue between positions 42 and 43. Thus, in addition to the contemplated insertions mentioned above, the following insertions between positions 42 and 43 are considered relevant:

X42X{A,T,G,S}, e.g., X42XA,X42XT,X42XG,X42XS;
X42X{D,E,K,R}, e.g., X42XD,X42XE,X42XK,X42XR;
X42X{H,V,C,N,Q}, e.g., X42XH,X42XV,X42XC,X42XN, X42XQ; and
X42X{F,I,L,M,P,W,Y}, e.g., X42XF,X42XI,X42XL, X42XM,X42XP, X42XW,X42XY.

In a preferred embodiment the insertion between positions 42 and 43 is selected from the group consisting of X42X{H, V,C,N,Q} in particular X42XN.

Examples of preferred variants are subtilase variants comprising the following insertions and substitutions: X99XD+X42XN as well as X99XD+X99A+X42XN. Particular preferred variants are subtilisin 309 variants comprising the following insertions and substitutions: S99SD+ L42LN as well as S99SD+S99A+L42LN .

With respect to insertions between position 99 and 100, it is—in a still further interesting embodiment of the present invention—preferred that the insertion is combined with a further insertion of at least one amino acid residue between positions 129 and 130. Thus, in addition to the contemplated insertions mentioned above, the following insertions between positions 129 and 130 are considered relevant:

X129X{A,T,G,S}, e.g., X129XA,X129XT,X129XG, X129XS;
X129X{D,E,K,R}, e.g., X129XD,X129XE,X129XK, X129XR;
X129X{H,V,C,N,Q}, e.g., X129XH,X129XV,X129XC, X129XN,X129XQ; and
X129X{F,I,L,M,P,W,Y}, e.g., X129XF,X129XI,X129XL, X129XM,X129XP, X129XW,X129XY.

In a preferred embodiment the insertion between positions 129 and 130 is selected from the group consisting of X129X{D,E,K,R}.

Examples of preferred variants are subtilase variants comprising the following insertions and substitutions: X99XD+X129XD as well as X99XD+X99A+X129XD. Particular preferred variants are subtilisin 309 variants comprising the following insertions and substitutions: S99SD+ P129PD as well as S99SD+S99A+P129PD.

It is well known in the art that a so-called conservative substitution of one amino acid residue to a similar amino acid residue is expected to produce only a minor change in the characteristic of the enzyme.

Table I below list groups of conservative amino acid substitutions.

TABLE I

Conservative amino acid substitutions

| Common Property | Amino Acid |
| --- | --- |
| Basic (positive charge) | K = lysine |
|  | H = histidine |
| Acidic (negative charge) | E = glutamic acid |
|  | D = aspartic acid |
| Polar | Q = glutamine |
|  | N = asparagine |
| Hydrophobic | L = leucine |
|  | I = isoleucine |
|  | V = valine |
|  | M = methionine |
| Aromatic | F = phenylalanine |
|  | W = tryptophan |
|  | Y = tyrosine |
| Small | G = glycine |
|  | A = alanine |
|  | S = serine |
|  | T = threonine |

According to this principle subtilase variants comprising conservative substitutions are expected to exhibit characteristics that are not drastically different from each other.

Based on the disclosed and/or exemplified subtilase variants herein, it is routine work for a person skilled in the art to identify suitable conservative modification(s) to these variants in order to obtain other subtilase variants exhibiting similarly improved wash-performance.

It is preferred that the parent subtilase belongs to the subgroups I-S1 and I-S2, especially subgroup I-S2, both for isolating enzymes from nature or from the artificial creation of diversity, and for designing and producing variants from a parent subtilase.

In relation to variants from subgroup I-S1, it is preferred to select a parent subtilase from the group consisting of BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of subgroup I-S1.

In relation to variants from subgroup I-S2 it is preferred to select a parent subtilase from the group consisting of BSAPRQ, BLS147 (BSAPRM, BAH101), BLSAVI (BSKSMK, BAALKP, BLSUBL), BYSYAB, BAPB92, TVTHER, and BSAPRS, or functional variants thereof having retained the characteristic of sub-group I-S2.

In particular, the parent subtilase is BLSAVI (Savinase®, NOVO NQRDISK A/S), and a preferred subtilase variant of the invention is accordingly a variant of Savinase®. Thus, particular interesting variants are subtilisin 309 variants, wherein 1. Ser has been inserted between positions 98 and 99, Ala in position 133 has been substituted with Glu, and Thr in position 143 has been substituted with Lys (BASBPN numbering); or 2. Asp has been inserted between positions 99 and 100 and Ser in position 99 has been substituted with Ala (BASBPN numbering); or 3. Thr has been inserted between positions 98 and 99, Tyr in position 167 has been substituted with Ala, Arg in position 170 has been substituted with Ser, and Ala in position 194 has been substituted with Pro (BASBPN numbering); or
4. Asp has been inserted between positions 99 and 100, Ser in position 99 has been substituted with Ala, and Pro has been inserted between positions 217 and 218 (BASBPN numbering).
5. Asp has been inserted between positions 99 and 100, Ser in position 99 has been substituted with Ala, and Pro has been inserted between positions 216 and 217 (BASBPN numbering).
6. Asp has been inserted between positions 99 and 100, Ser in position 99 has been substituted with Ala, and Asp-Pro has been inserted between positions 216 and 217 (BASBPN numbering).
7. Asp has been inserted between positions 99 and 100, Ser in position 99 has been substituted with Ala, and Asp has been inserted between positions 129 and 130 (BASBPN numbering).
8. Asp has been inserted between positions 99 and 100, and Asn has been inserted between positions 42 and 43 (BASBPN numbering).
9. Asp has been inserted between positions 99 and 100, Ser in position 99 has been substituted with Ala, and Asn has been inserted between positions 42 and 43 (BASBPN numbering).
10. Arg has been inserted between posiions 99 and 100, and Ser in position 99 has been substituted with Thr.
11. Asp has been inserted between positions 99 and 100, Ser in position 99 has been substituted with Ala, and Pro in position 131 has been substituted with Thr.

The present invention also encompass use of any of the above mentioned subtilase variants in combination with any other modification to the amino acid sequence thereof. Especially combinations with other modifications known in the art to provide improved properties to the enzyme are envisaged. The art describes a number of subtilase variants with different improved properties and a number of those are mentioned in the "Background of the invention" section herein (vide supra). Those references are disclosed here as references to identify a subtilase variant, which advantageously can be combined with a subtilase variant described herein.

Such combinations comprise the positions: 222 (improves oxidation stability), 218 (improves thermal stability), substitutions in the Ca-binding sites stabilizing the enzyme, e.g. position 76, and many other apparent from the prior art.

In further embodiments a subtilase variant described herein may advantageously be combined with one or more modification(s) in any of the positions:

27, 36, 56, 76, 87, 97, 101, 103, 104, 120, 123, 159, 167, 170, 206, 218, 222, 224, 232, 235, 236, 245, 248, 252 and 274.

Specifically the following BLSAVI, BLSUBL, BSKSMK, and BAALKP variants are considered appropriate for combination:

K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A.

Furthermore variants comprising any of the variants S101G+V104N, S87N+S101G+V104N, K27R+V104Y+N123S+T274A, N76D+S103A+V104I or N76D+V104A or other combinations of these mutations (V104N, S101G, K27R, V104Y, N123S, T274A, N76D, V104A) or S101G+S103A+V104I+G159D+A232V+Q236H+Q245R+N248D+N252K in combination with any one or more of the modification(s) mentioned above exhibit improved properties.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

As mentioned above, the variants disclosed herein are only inhibited by trypsin inhibitor type IV-0 to a limited extent and, consequently, they exhibit excellent wash performance on egg stains. Therefore, in order to enable the skilled person—at an early stage of his development work—to select effective and preferred variants for this purpose, the present inventors have provided a suitable preliminary test, which can easily be carried out by the skilled person in order to initially assess the performance of the variant in question.

Thus, the "Ovo-inhibition Assay" disclosed in Example 4 herein may be employed to initially assess the potential of a selected variant. In other words, the "Ovo-inhibition Assay" may be employed to assess whether a selected variant will be inhibited, and to what extent, by the trypsin inhibitor type IV-0. Using this test, the suitability of a selected variant to remove egg stains can be assessed, the rationale being that if a selected variant is strongly inhibited by trypsin inhibitor type IV-0, it is normally not necessary to carry out further test experiments.

Therefore, a variant which is particular interesting for the use described herein, is a variant which—when tested in the "Ovo-inhibition Assay" described in Example 4 herein—has a Residual Activity of at least 10%, e.g. at least 15%, such as at least 20%, preferably at least 25%, such as at least 30%, more preferably at least 35%. In a particular interesting embodiment of the invention, the variant has a Residual Activity of at least 40%, such as at least 45%, e.g. at least 50%, preferably at least 55%, such as at least 60%, more preferably at least 65%, such as at least 70%, even more preferably at least 75%, such as at least 80%, e.g. at least 90%, when tested in the "Ovo-inhibition Assay" described in Example 4 herein.

Evidently, it is preferred that the variant of the invention fulfils the above criteria on at least the stated lowest level, more preferably at the stated intermediate level and most preferably on the stated highest level.

Alternatively, or in addition to the above-mentioned assay, the suitability of a selected variant may be tested in the "Model Detergent Wash Performance Test" disclosed in Example 3 herein. The "Model Detergent Wash Perfomance Test" may be employed to assess the ability of a variant, when incorporated in a standard detergent composition, to remove egg stains from a standard textile as compared to a reference system, namely the parent subtilase (incorporated in the same model detergent system and tested under identical conditions). Using this test, the suitability of a selected variant to remove egg stains can be initially investigated, the rationale being that if a selected variant does not show a significant improvement in the test compared to the parent subtilase, it is normally not necessary to carry out further test experiments.

Therefore, variants which are particular interesting for the use described herein, are such variants which, when tested in a model detergent composition comprising

| | |
|---|---|
| 6.2% | LAS (Nansa 80S) |
| 2% | Sodium salt of $C_{16}$–$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| | Water (balance) | as described in the "Model Detergent Wash Performance Test" disclosed in Example 3 herein, shows an improved wash performance on egg stains as compared to the parent subtilase tested under identical conditions.

The improvement in the wash performance may be quantified by employing the so-called "Performance Factor" defined in Example 3, herein.

In a very interesting embodiment of the invention, the variant of the invention, when tested in the "Wash Performance Test" has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the variant of the invention fulfils the above criteria on at least the stated lowest level, more preferably at the stated intermediate level and most preferably on the stated highest level.

As indicated above, the present invention also provides novel subtilase variants. It will be understood that details and particulars concerning the novel subtilase variant aspects of the invention will be the same or analogous to the details and particulars of the variants discussed above in connection with the use aspect of the invention. This means that whenever appropriate, the statements concerning the use (e.g. preferred insertions and substitutions, etc.) discussed in detail herein, apply mutatis mutandis to the novel subtilase variants according to the invention as well as to the method aspect and the cleaning and detergent composition aspect of the invention.

Producing a Subtilase Variant

Many methods for cloning a subtilase and for introducing insertions into genes (e.g. subtilase genes) are well known in the art, cf. the references cited in the "BACKGROUND OF THE INVENTION" section.

In general standard procedures for cloning of genes and introducing insertions (random and/or site directed) into said genes may be used in order to obtain a subtilase variant of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further, a subtilase variant may be constructed by standard techniques for artificial creation of diversity, such as by DNA shuffling of different subtilase genes (WO 95/22625; Stemmer WPC, Nature 370:389–91 (1994)). DNA shuffling of e.g. the gene encoding subtilisin 309 with one or more partial subtilase sequences identified in nature to comprise an active site (b) loop regions longer than the active site (b) loop of subtilisin 309, will after subsequent screening for improved wash performance variants, provide subtilase variants suitable for the purposes described herein.

Expression Vectors

A recombinant expression vector comprising a DNA construct encoding the enzyme of the invention may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid.

Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretary signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Cleaning and Detergent Compositions

In general, cleaning and detergent compositions are well described in the art and reference is made to WO 96/34946; WO 97/07202; WO 95/30011 for further description of suitable cleaning and detergent compositions.

Furthermore the examples herein demonstrate the improvements in wash performance on egg stains for a number of subtilase variants.

Detergent Compositions

The subtilase variant may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising a subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a *Pseudomonas lipase*, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (α and/or β) include those of bacterial or fungal origin. Chemically modified or protein engineered mutants are included. Amylases include, for example, α-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition typically comprises one or more surfactants, which may be non-ionic including semi-polar and/or anionic and/or cationic and/or zwitterionic. The surfactants are typically present at a level of from 0.1% to 60% by weight. When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriamine-pentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202 which is hereby incorporated as reference.

The invention is described in further detail in the following examples, which are not in any way intended to limit the scope of the invention as claimed.

In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF GmbH |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula δ-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF Gmbh |
| Zeolite A: | Hydrated Sodium Aluminosilicate of formula $Na_{12}(AlO_2SiO_2)_{12}.27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Percarbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N,N'-disuccinic acid, [S,S] isomer in the form of the sodium salt |
| Suds Suppressor: | 25% paraffin wax Mpt 50° C., 17% hydrophobic silica, 58% paraffin oil |
| Granular Suds suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulphonate | 0.1 |
| Minors | up to 100% |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Powder Automatic Dishwash Composition I

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |

Powder Automatic Dishwash Composition II

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid co-polymer) | 6–25% |
| Enzymes | 0.0001–0.1% |
| Perfume | 0.1–0.5% |
| Water | 5–10 |

Powder Automatic Dishwash Composition III

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetyl ethylene diamine (TAED) | 0–6% |
| Maleic acid/acrylic acid copolymer | 0–5% |

-continued

| | |
|---|---|
| Clay | 1–3% |
| Polyamino acids | 0–20% |
| Sodium polyacrylate | 0–8% |
| Enzymes | 0.0001–0.1% |

Powder Automatic Dishwash Composition IV

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

Powder Automatic Dishwash Composition V

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |

Powder and Liquid Dishwash Composition with Cleaning Surfactant System VI

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |

-continued

| | |
|---|---|
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |

Non-aqueous Liquid Automatic Dishwshing Composition VII

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

Non-aqueous Liquid Dishwashing Composition VIII

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

Thixotropic Liquid Automatic Dishwashing Composition IX

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

Liquid Automatic Dishwashing Composition X

| Alcohol ethoxylate | 0–20% |
| --- | --- |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |

Liquid Automatic Dishwashing Composition Containing Protected Bleach Particles XI

| Sodium silicate | 5–10% |
| --- | --- |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

XII: Automatic dishwashing compositions as described in I, II, III, IV, VI and X, wherein perborate is replaced by percarbonate.

XIII: Automatic dishwashing compositions as described in I–VI, which additionally contain a manganese catalyst. The manganese catalyst may, e.g., be one of the compounds described in "Efficient manganese catalysts for low-temperature bleaching", *Nature*, (1994), 369, 637–639.

Materials and Methods

Textiles

WFK10N standard textile pieces (egg stains) were obtained from WFK Testgewebe GmbH, Christenfeld 10, D-41379 Brübggen-Bracht, Germany.

Strains

B. subtilis DN1885 (Diderichsen et al., 1990).

B. lentus 309 and 147 are specific strains of *Bacillus lentus*, deposited with the NCIB and accorded the accession numbers NCIB 10309 and 10147, and described in U.S. Pat. No. 3,723,250 incorporated by reference herein.

E. coli MC 1000 (M. J. Casadaban and S. N. Cohen (1980); *J. Mol. Biol.* 138 179–207), was made r$^-$,m$^+$ by conventional methods and is also described in U.S. patent application Ser. No. 039,298.

Plasmids pJS3 (SEQ ID NO:60): *E. coli—B. subtilis* shuttle vector containing a synthetic gene encoding for subtilase 309 (Described by Jacob Schiødt et al. in Protein and Peptide letters 3:39–44 (1996)).

pSX222: *B. subtilis* expression vector (described in WO 96/34946).

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restriction endonucleases, ligases etc., are obtained from New England Biolabs, Inc.

Proteolytic Activity

In the context of this invention proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15 minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitro-phenol, which is described in the Journal of American Oil Chemists Society, Rothgeb, T. M., Goodlander, B. D., Garrison, P. H., and Smith, L. A., (1988).

Fermentation

Fermentations for the production of subtilase enzymes were performed at 30° C. on a rotary shaking table (300 r.p.m.) in 500 ml baffled Erlenmeyer flasks containing 100 ml BPX medium for 5 days.

Consequently in order to make an e.g. 2 liter broth 20 Erlenmeyer flasks were fermented simultaneously.

| MEDIA: BPX Medium Composition (per liter) | |
| --- | --- |
| Potato starch | 100 g |
| Ground barley | 50 g |
| Soybean flour | 20 g |
| Na$_2$HPO$_4$ × 12 H$_2$O | 9 g |
| Pluronic | 0.1 g |
| Sodium caseinate | 10 g |

The starch in the medium is liquefied with α-amylase and the medium is sterilized by heating at 120° C. for 45 minutes. After sterilization the pH of the medium is adjusted to 9 by addition of NaHCO$_3$ to 0.1 M.

EXAMPLE 1

Construction and Expression of Enzyme Variants

Site-directed Mutagenesis

Subtilase 309 (savinase®) site-directed variants of the invention comprising specific insertions and comprising specific substitutions were made by traditional cloning of DNA fragments (Sambrook et al., Molecular Cloning: A Laboratory Manual, 2nd Ed., Cold Spring Harbor, 1989) produced by PCR with oligos containing the desired insertions (see below).

The template plasmid DNA was pJS3 (see below), or an analogue of this containing a variant of Subtilase 309.

Insertions and substitutions were introduced by oligo directed mutagenesis to the construction of variants.

The Subtilase 309 variants were transformed into *E. coli*. DNA purified from a over night culture of these transformants were transformed into *B. subtilis* by restriction endonuclease digestion, purification of DNA fragments, ligation, transformation of *B. subtilis*. Transformation of *B. subtilis* was performed as described by Dubnau et al., 1971, J. Mol. Biol. 56, pp. 209–221.

Site-directed Mutagenesis in Order to Introduce Insertions and Substitutions in a Specific Region The overall strategy to used to perform site-directed mutagenesis was:

Mutagenic primers (oligonucleotides) were synthesized corresponding to the DNA sequence flanking the sites of insertion and substitutions, separated by the DNA base pairs defining the insertions and substitutions.

Subsequently, the resulting mutagenic primers were used in a PCR reaction with the modified plasmid pJS3 (see above). The resulting PCR fragment was purified and extended in a second PCR-reaction, the resulting PCR product was purified and either cloned into the *E. coli—B. subtilis* shuttle vector (see below) or extended in a third PCR-reaction before being digested by endonucleases and cloned into the *E. coli—B. subtilis* shuttle vector (see below). The PCR reactions are performed under normal conditions.

Following this strategy insertions and substitutions were introduced in subtilisin 309 wherein insertions and substitutions were introduced according to the below table. The primers used for each PCR step are shown as well as the cloning sites used.

Following the above strategy a detailed example follows:

Two insertions and one substitution were introduced in subtilisin 309 wherein the insertions were introduced in positions 99 (*99aD) and 217 (217aP) respectively and a substitution was introduced in position S99A (see below).

The insertion and substitution at position 99 was introduced by a mutagenic primer (5' CCG AAC CTG AAC CAT CCG CGG CCC CTA GGA CTT AAA CAG C 3' (sense)) (SEQ ID NO:71) were used in a PCR re-action with an opposite primer (5' GAG TTA AGC CCA GAA GAT GTG GAC GCG 3' (antisense)) (SEQ ID NO:83).

The produced PCR fragment were extended towards the C-terminal of subtilisin 309 by a second round of PCR introducing the insertion at position 217 with primer; 5' CAT CGA TGT ACC GTT TGG TAA GCT GGC ATA TGT TG 3' (SEQ ID NO:94). The second round PCR product were extended towards the C-terminal of subtilisin 309 by a third round of PCR with primer; 5' AAC CGC ACA GCG TTT TTT TAT TGA TTA ACG CGT TGC 3' (SEQ ID NO;105), situated downstream at the Mlu I site in pJS3. All PCR reactions used plasmid pJS3 as template. The extended DNA-fragment resulting from third round PCR was cloned into the Sal I- and Mlu I-sites of the modified plasmid pJS3 (see above).

The plasmid DNA was transformed into *E. coli* by well-known techniques and one *E. coli* colony were sequenced to confirm the mutation designed.

All other variants were constructed in an analogous manner.

In order to purify a subtilase variant of the invention, the *B. subtilis* pJS3 expression plasmid comprising a variant of the invention was transformed into a competent *B. subtilis* strain and was fermented as described above in a medium containing 10 µg/ml Chloramphenicol (CAM).

Primers and cloning sites:

| Variant | Step 1 PCR primers | Step 2 PCR primers | Step 3 PCR | Cloning site |
|---|---|---|---|---|
| S99SR + S99T | Sense: (5' CAG AAG ATG TGG ACG CGC TTG 3') (SEQ ID NO:2) Antisense: (5' TGA ACC GCT GGT GGG GCC TAG GAC TTT AAC AG 3') (SEQ ID NO:7) | Sense: (step 1 PCR product) AntiSense: (5' GAT TAA CGC GTT GCC GCT TCT G 3') (SEQ ID NO:8) | | HindIII-XbaI |
| S99SQ + S99T | Sense: (5' CAG AAG ATG TGG ACG CGC TTG 3') (SEQ ID NO:9) Antisense: (5' GAC CGA ACC TGA ACC CTG AGT GGC GCC TAG GAC 3') (SEQ ID NO:10) | Sense: (step 1 PCR product) Antisense: (5' GAT TAA CGC GTT GCC GCT TCT G 3') (SEQ ID NO:11) | | HindIII-XbaI |
| S99SD + M222S | Sense: (5' GAG TTA AGC CCA GAA GAT GTG GAC GCG 3') (SEQ ID NO:12) Antisense: (5' GAC CGA | Sense: (step 1 PCR product) Antisense: (5' AGG AGT AGC CGA CGA TGT ACC GTT TAA GC 3') | | SalI-MluI |

Primers and cloning sites:

| Variant | Step 1 PCR primers | Step 2 PCR primers | Step 3 PCR | Cloning site |
|---|---|---|---|---|
| | ACC TGA ACC ATC GCT CGC CCC TAG GAC 3') (SEQ ID NO:13) | (SEQ ID NO:14) | | |
| L96LA + A98T + A108C + A138C | Sense: (5' GAG TTA AGC CCA GAA GAT GTG GAC GCG 3') (SEQ ID NO:15) Antisense: (5' CCA TTC CAA TCC CTG GCA AAT CGA GCT GAC CGA ACC TGA ACC GCT GGT ACC CGC TAG GAC TTT AAT AGC G 3') (SEQ ID NO:17 | Sense: (step 1 PCR product) Antisense: (5' AAC GCC TCT AGA AGT CGC GCT ATT AAC ACA TTG CTC GAG TGT GG 3') (SEQ ID NO:18) | Sense: (step 2 PCR product) Antisense: (5' AAC CGC ACA GCG TTT TTT TAT TGA TTA ACG CGT TGC 3') (SEQ ID NO:19) | SalI-MluI |
| A98AT + G97D | Sense: (5' CAG AAG ATG TGG ACG CGC TTG 3') (SEQ ID NO:20) Antisense: (5' AAC CGC TGG TGG CGT CTA GGA CTT TAA CAG CG 3') (SEQ ID NO:21) | Sense: (step1 PCR product) Antisense: (5' GAT TAA CGC GTT GCC GCT TCT G 3') (SEQ ID NO:22) | | HindIII-XbaI |
| A98AT + G97E | Sense: (5' CAG AAG ATG TGG ACG CGC TTG 3') (SEQ ID NO:23) Antisense: (5' AAC CGC TGG TGG CTT CTA GGA CTT TAA CAG CG 3') (SEQ ID NO:24) | Sense: (step 1 PCR product) Antisense: (5' GAT TAA CGC GTT GCC GCT TCT G 3') (SEQ ID NO:25) | | HindIII-XbaI |
| S99SA | Sense: (5' GAG TTA AGC CCA GAA GAT GTG GAC GCG 3') (SEQ ID NO:26) Antisense: (5' ACC GAA CCT GAA CCT GCG CTC GCC CCT AGG 3') (SEQ ID NO:28) | Antisense: K828 | | HindIII-XbaI |
| S99SE + S99T | Sense: (5' CAG AAG ATG TGG ACG CGC TTG 3') (SEQ ID NO:29) Antisense: | Antisense: (5' GAT TAA CGC GTT GCC GCT TCT G 3') (SEQ ID NO:31) | | HindIII-XbaI |

-continued

Primers and cloning sites:

| Variant | Step 1 PCR primers | Step 2 PCR primers | Step 3 PCR | Cloning site |
|---|---|---|---|---|
| | (5' GAC CGA ACC TGA GCC CTC GGT GGC GCC TAG GAC 3') (SEQ ID NO:30) | | | |
| S99SD + S99A + A133E | Sense: (5' CCC TTC GCC AAG TGA GAC TCT CGA GCA AGC TG 3') (SEQ ID NO:32) Antisense: (5' AAC CGC ACA GCG TTT TTT TAT TGA TTA ACG CGT TGC 3') (SEQ ID NO:33) | Sense: (5' AAA GTC CTA GGG GCC GCC GAC GGT TCA GGT TCG GTC AGC 3') (SEQ ID NO:34) Antisense: (step 1 PCR product) | Sense: (5' GAG TTA AGC CCA GAA GAT GTG GAC GCG 3') (SEQ ID NO:35) Antisense: (step 2 PCR product) | SalI-MluI |
| S99SD + S99A + T143K | Sense: (5' TGT TAA TAG CGC GAA ATC CAG AGG CGT TCT TG 3') (SEQ ID NO:36) Antisense: (5' AAC CGC ACA GCG TTT TTT TAT TGA TTA ACG CGT TGC 3') (SEQ ID NO:37) | Sense: (5' AAA GTC CTA GGG GCC GCC GAC GGT TCA GGT TCG GTC AGC 3') (SEQ ID NO:39) Antisense: (step 1 PCR product) | Sense: (5' GAG TTA AGC CCA GAA GAT GTG GAC GCG 3') (SEQ ID NO:40) Antisense: (step 2 PCR product) | SalI-MluI |
| S99SD + S99A + S216SP | Sense: (5' GAG TTA AGC CCA GAA GAT GTG GAC GCG 3') (SEQ ID NO:41) Antisense: (5' CCG AAC CTG AAC CAT CCG CGG CCC CTA GGA CTT TAA CAG C 3') (SEQ ID NO:42) | Sense: (step 1 PCR product) Antisense: (5' GAT GTA CCG TTT AAA GGG CTG GCA TAT GTT GAA CC 3') (SEQ ID NO:43) | Sense: (step 2 PCR product) Antisense: (5' AAC CGC ACA GCG TTT TTT TAT TGA TTA ACG CGT TGC 3') (SEQ ID NO:44) | SalI-MluI |
| S99SD + S99A + S216SDP | Sense: (5' GAG TTA AGC CCA GAA GAT GTG GAC GCG 3') SEQ ID NO:45) Antisense: (5' CCG AAC CTG AAC CAT CCG CGG CCC CTA GGA CTT TAA CAG C) SEQ ID NO:46) | Sense: (step 1 PCR product) Antisense: (5' GTA CCG TTT AAA GGA TCG CTG GCA TAT GTT GAA CC 3') (SEQ ID NO:47) | Sense: (step 2 PCR product) Antisense: (5' AAC CGC ACA GCG TTT TTT TAT TGA TTA ACG CGT TGC 3') (SEQ ID NO:48) | SalI-MluI |
| S99SD + S99A + P129PD | Sense: (5' GAG TTA AGC CCA GAA GAT GTG GAC GCG 3') (SEQ ID NO:50) Antisense: (5' CCG AAC CTG AAC CAT | Sense: (step 1 PCR product) Antisense: (5' GTG TGG CAC TTG GCG AGT CAG GGC TTC CTA AAC TC 3') (SEQ | Sense: (step 2 PCR product) Antisense: (5' AAC CGC ACA GCG TTT TTT TAT TGA TTA ACG CGT TGC 3') | SalI-MluI |

-continued

Primers and cloning sites:

| Variant | Step 1 PCR primers | Step 2 PCR primers | Step 3 PCR | Cloning site |
|---|---|---|---|---|
| | CCG CGG CCC CTA GGA CTT TAA CAG C 3') (SEQ ID NO:51) | ID NO:52) | (SEQ ID NO:53) | |
| S99SD + S99SA + P129PR | Sense: (5' GAG TTA AGC CCA GAA GAT GTG GAC GCG 3') (SEQ ID NO:54) Antisense: (5' CCG AAC CTG AAC CAT CCG CGG CCC CTA GGA CTT TAA CAG C 3') (SEQ ID NO:55) | Antisense: (5' GTG TGG CACT TGG CGA TCG AGG GCT TCC TAA ACT C 3') (SEQ ID NO:56) | Sense: (step 2 PCR product) Antisense: (5' AAC CGC ACA GCG TTT TTT TAT TGA TTT TAT TGA TTA ACG CGT TGC 3') NO:57) | SalI-MluI |
| S99SD + S99A + L217F + A228V + A230V | Sense: (5' GAG TTA AGC CCA GAA GAT GTG GAC GCG 3') (SEQ ID NO:58) Antisense: (5' CCG AAC CTG AAC CAT CCG CGG CCC CTA GGA CTT TAA CAG C 3') (SEQ ID NO:59) | Antisense: (5' (AAG GGC GGC CAC ACC TAC AAC ATG AGG AGT AGC CAT CGA TGT ACC GTT AAA GCT GGC ATA TGT TGA AC 5') (SEQ ID NO:61) | Sense: (step 2 PCR product) Antisense: (5' AAC CGC ACA GCG TTT TTT TAT TGA TTA ACG CGT TGC 3') (SEQ ID NO:62) | SalI-MluI |
| S99SD + S99A + L217LP | Sense: (5' GAG TTA AGC CCA GAA GAT GTG GAC GCG 3') (SEQ ID NO:63) Antisense: (5' CCG AAC CTG AAC CAT CCG CGG CCC CTA GGA CTT TAA CAG C 3') (SEQ ID NO:64) | Antisense: (5' CAT CGA TGT ACC GTT TGG TAA GCT GGC ATA TGT TG 3') (SEQ ID NO:65) | Sense: (step 2 PCR product) Antisense: (5' AAC CGC ACA GCG TTT TTT TAT TGA TTA ACG CGT TGC 3') (SEQ ID NO:66) | SalI-MluI |
| G97GI + S99T | Sense: (5' GCT GTT AAA GTC CTA GGG ATC GCG ACT GGT TCA GGT TCG GTC AGC 3') (SEQ ID NO:76) Antisense: (5' GAT TAA CGC GTT GCC GCT TCT G 3') (SEQ ID NO:68) | | | AvrII-XbaI |
| A98AS + A133E + T143K | Sense: (5' GTT AAA GTC CTA GGG GCG TCG AGC GGT TCA GGT TCG GTC 3') (SEQ ID NO:69) Antisense: (5'C aag AAC GCC TCT AGA TTT CGC GCT ATT AAC AGC TTG CTC | | | AvrII-XbaI |

-continued

Primers and cloning sites:

| Variant | Step 1 PCR primers | Step 2 PCR primers | Step 3 PCR | Cloning site |
|---|---|---|---|---|
| A98AG | GAG TGT TTC ACT TGG CGA AGG GCT TCC 3') (SEQ ID NO:70) Sense: (5' GCT GTT AAA GTC CTA GGG GCG GGT AGC GGT TCA GGT TCG GTC 3') (SEQ ID NO:72) Antisense: (5' GAT TAA CGC GTT GCC GCT TCT G 3' 3') (SEQ ID NO:73) | | | AvrII-XbaI |
| A98AS + R45K + S105G | Sense: (5' GTC CTC GAT ACA GGG ATA TCC ACT CAT CCA GAT CTA AAT ATT AAA GGT GGC GCA AGC TTT GTA C 3') (SEQ ID NO:74) Antisense: (5' CGC CCC TAG GAC TTT AAC AGC 3') (SEQ ID NO:75) | Sense: (5' GCT GTT AAA GTC CTA GGG GCG TCG AGC GGT TCA GGT TCG GTC GGG TCG ATT GCC CAA GGA TTG 3') (SEQ ID NO:76) Antisense: (5' GAT TAA CGC GTT GCC GCT TCT G 3' 3') (SEQ ID NO:77) | Sense: (step 1 PCR product) Antisense: (step 2 PCR product) | EcoRV-XbaI |
| A98ASGTG | Sense: (5' GCT GTT AAA GTC CTA GGG GCG TCG GGC ACT GGC AGC GGT TCA GGT TCG GTC 3') (SEQ ID NO:78) Antisense: (5' GAT TAA CGC GTT GCC GCT TCT G 3') (SEQ ID NO:79) | | | AvrII-XbaI |
| A98AP + A98G + S99A | Sense: (5' GCT GTT AAA GTC CTA GGG GGC CCAGCC GGT TCA GGT TCG GTC AGC 3') (SEQ ID NO:80) Antisense: (5' GAT TAA CGC GTT GCC GCT TCT G 3') (SEQ ID NO:81) | | | AvrII-XbaI |
| A98AI + A98G + S99H + G100S + S101A | Sense: (5' GCT GTT AAA GTC CTA GGG GGC ATC CAT TCG GCA GGT TCG GTC AGC TCG ATT 3') (SEQ ID NO:82) Antisense: | | | AvrII-XbaI |

-continued

Primers and cloning sites:

| Variant | Step 1 PCR primers | Step 2 PCR primers | Step 3 PCR | Cloning site |
|---|---|---|---|---|
| S99SD + S99A | (5' gat taa CGC GTT GCC GCT TCT G 3') (SEQ ID NO:84) Sense: (5' GCT GTT AAA GTC CTA GGG GCG GCA GAC GGT TCA GGT TCG GTC AGC 3') (SEQ ID NO:85) Antisense: (5' GAT TAA CGC GTT GCC GCT TCT G 3') (SEQ ID NO:86) | | | AvrII-XbaI |
| S99SD + S99A + P131T | Sense: (5' GCT GTT AAA GTC CTA GGG GCG GCA GAC GGT TCA GGT TCG GTC AGC | | | AvrII-XbaI |
| L96LA | Sense: (5' GAG TTA AGC CCA GAA GAT GTG GAC GCG 3') (SEQ ID NO:89) Antisense: (5' AAC CGC TCG CCC CTG CTA GGA CTT TAA CAG 3') (SEQ ID NO:90) | Sense: (step 1 PCR product) Anstisense: (5' AAC CGC ACA GCG TTT TTT TAT TGA TTA ACG CGT TG C 3') (SEQ ID NO:91) | | SalI-MluI |
| S99SN | Sense: (5' GAG TTA AGC CCA GAA GAT GTG GAC GCG 3') (SEQ ID NO:92) Antisense: (5' GAC CGA ACC TGA ACC GTT GCT CGC CCC TAG GAC 3') (SEQ ID NO:93) | Sense: (step 1 PCR product) Anstisense: (5' AAC CGC ACA GCG TTT TTT TAT TGA TTA ACG CGT TG C 3') (SEQ ID NO:95) | | SalI-MluI |
| S99SD | Sense: (5' GAG TTA AGC CCA GAA GAT GTG GAC GCG 3') (SEQ ID NO:96) Antisense: (5' GAC CGA ACC TGA ACC ATC GCT CGC CCC TAG GAC 3') (SEQ ID NO:97) | Sense: (step 1 PCR product) Anstisense: (5' AAC CGC ACA GCG TTT TTT TAT TGA TTA ACG CGT TG C 3') (SEQ ID NO:98) | | SalI-MluI |
| S99SE | Sense: (5' GAG TTA AGC CCA GAA GAT GTG GAC GCG 3') (SEQ ID NO:99 Antisense: (5' GAC CGA ACC TGA ACC | Sense: (step 1 PCR product) Antisense: (5' AAC CGC ACA GCG TTT TTT TAT TGA TTA ACG CGT TG C 3') | | SalI-MluI |

-continued

Primers and cloning sites:

| Variant | Step 1 PCR primers | Step 2 PCR primers | Step 3 PCR | Cloning site |
|---|---|---|---|---|
| | TTC GCT CGC CCC TAG GAC 3') (SEQ ID NO:100) | (SEQ ID NO:101) | | |
| A98AT + Y167A + R170S + A194P | Sense: (5' GAG TTA AGC CCA GAA GAT GTG GAC GCG 3') (SEQ ID NO:102) Antisense: (5' TGT GTA AAG TAA CTC ATT TGG TGA GCC AG 3') (SEQ ID NO:103) | Sense: (step 1 PCR product) Anstisense: (5' CCG ACT GCC ATT GCG TTC GCA TAC GAC GCC GGG GCG CTG ATT GAG CCT GCA C 3') (SEQ ID NO:104) | Sense: (step 2 PCR product) Anstisense: (5' CTG CAC GTT TAC CCC GGG TGC GAC AAT GTC AAG GCC TGG GCC ATA CTG TG 3') (SEQ ID NO:3) | SalI-XmaI |
| S99SD + L42LN + S99A | Sense: (5' CTC GAT ACA GGG ATA TCC ACT CAT CCA GAT CTA AAC AAT ATT CGT GGT GGC G 3') (SEQ ID NO:4) Antisense: (5' CCG AAC CTG AAC CAT CCG CGG CCC CTA GGA CTT TAA CAG C 3') (SEQ ID NO:5) | Sense: (step 1 PCR product) Anstisense: (5' ACA GCG TTT ACA GCG TTT TTT TAT TGA TTA ACG CGT TGC 3') (SEQ ID NO:6) | | EcoRV-MluI |

EXAMPLE 2
Purification of Enzyme Variants

This procedure relates to purification of a 2 liter scale fermentation for the production of the subtilases of the invention in a Bacillus host cell.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 litres of the same buffer (0–0.2 M sodium chloride in case of Subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and fermentation, and the above isolation procedure the following subtilisin 309 variants were produced and isolated:

Position 96 Insertion Variants
  L96LA
  L96LA+A98T+A108C+A138C
Position 97 Insertion Variants
  G97GI+S99T
Position 98 Insertion Variants
  A98AS+A133E+T143K
  A98AT+G97D
  A98ATGTG
  A98AG
  A98AS+R45K+S105G
  A98AT+G97E
  A98ASGTG
  A98AP+A98G+S99A
  A98AT+Y167A+R170S+A194P
  A98AI+A98G+S99H+G100S+S101A
Position 99 Insertion Variants
  S99SD+S99A
  S99SA
  S99SE+S99T S99SD+S99A+A133E
S99SD+S99A+T143K
S99SD
S99SE
S99SD+S99A+S216SP
S99SD+S99A+S216SDP
S99SD+S99A+P129PD
S99SD+S99A+P129PR
S99SD+S99A+L217F+A228V+A230V
S99SD+S99A+L217LP
S99SD+S99A+L42LN
S99SR+S99T
S99SQ+S99T
S99SD+M222S
S99SD+N76D+A194P+A230V
S99SN
S99SD+S99A+P131T

EXAMPLE 3

The "Model Detergent Wash Performance Test"

In order to asses the wash performance of selected subtilase variants in a standard detergent composition, standard washing experiments may be performed using the below experimental conditions:

| Detergent: | Model detergent |
|---|---|
| Detergent dosage | 4.0 g/l |
| pH | 10.1 |
| Wash time | 20 min |
| Temperature: | 30° C. |
| Water hardness: | 150° dH |
| Enzyme concentration: | 10 nm (in the detergent solution) |
| Test system: | 10 ml beakers with a stirring rod |
| Textile/volume: | 5 textile pieces (Ø 2.5 cm)/50 ml detergent solution |
| Test material: | WFK10N (egg stains) |

The composition of the model detergent is as follows:

| | |
|---|---|
| 6.2% | LAS (Nansa 80S) |
| 2% | Sodium salt of $C_{16}$–$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| | Water (balance) | pH of the detergent solution is adjusted to 10.1 by addition of HCl or NaOH. Water hardness is adjusted to 15° dH by addition of $CaCl_2$ and $MGCl_2$ ($Ca^{2+}$:$Mg^{2+}$=4:1) to the test system. After washing the textile pieces were flushed in tap water and air-dried.

Measurement of the reflectance ($R_{variant}$) on the test material is performed at 460 nm using a Macbeth ColorEye 7000 photometer (Macbeth, Division of Kollmorgen Instruments Corporation, Germany). The measurements are performed accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of the parent enzyme is tested. The subsequent measurement of the reflectance ($R_{parent}$) is performed as described right above.

The wash performance is evaluated by means of the Performance Factor (P) which is defined in accordance with the below formula:

$$P = (R_{variant} - R_{blank}) - (R_{parent} - R_{blank})$$

$$= R_{variant} - R_{parent}.$$

Using the above test method the following results were obtained:

| Enzyme | R (460 nm) | P |
|---|---|---|
| Blank (no enzyme) | 40.5 | — |
| Parent (Savinase ®) | 40.7 | — |
| S99SD + S99A | 43.2 | 2.5 |
| S99SA | — | 2.0 |
| S99SE + S99T | — | 2.0 |
| A98AS + A133E + T143K | 45.1 | 4.4 |
| A98AT + G97D | — | 1.5 |
| A98ATGTG | — | 1.6 |
| A98AG | — | 1.7 |
| A98AS + R45K + S105G | — | 1.8 |
| A98AT + G97E | — | 2.0 |
| A98ASGTG | — | 2.1 |
| A98AP + A98G + S99A | — | 2.3 |

As it appears, the subtilase variants exhibit improved wash performance on egg stains in comparison to the parent subtilase, i.e. Savinase®.

EXAMPLE 4

The "Ovo-inhibition Assays"

The below inhibition assay is based on the principle that the subtilase variant to be tested will catalyse the hydrolysis of a peptide-pNA bond, thereby releasing the yellow pNA, which may conveniently be followed at 405 nm. The amount of released pNA after a given period of time is a direct measure of the subtilase activity. By carrying out such hydrolysis experiments with and without inhibitor, respectively, it is possible to obtain a quantitative measure for the degree to which a certain subtilase variant is inhibited.

| Reaction conditions: | |
|---|---|
| Enzyme concentration: | 0.0003 mg/ml |
| Conc. of trypsin inhibitor type IV-0: | 0.0015 mg/ml |
| Initial substrate concentration: | 0.81 mM |
| Reaction time: | 11 min |
| Assay temperature: | 25° C. |
| Assay pH: | 8.6 |
| Absorbance measured at: | 405 nm |

Assay Solutions

Substrate solution (2 mM): 500 mg Suc—Ala—Ala—Pro—Phe—pNA is dissolved in 4 ml DMSO (200 mM). This solution is diluted 100 times with the buffer solution described below. The concentration of substrate in the resulting substrate solution is 2 mM.

Inhibitor solution (0.005 mg/ml): 5 mg trypsin inhibitor type IV-0 (Sigma T-1886) is dissolved in 10 ml water. This solution is dissolved 100 times with the buffer solution described below. The concentration of inhibitor in the resulting inhibitor solution is 0.005 mg/ml.

Enzyme solution (0.001 mg/ml): 1 mg enzyme is dissolved in 10 ml water. This solution is dissolved 100 times with the buffer solution described below. The concentration of enzyme in the resulting enzyme solution is 0.001 mg/ml.

Buffer solution (pH 8.6): 15.7 mg Tris is dissolved in an appropriate amount of water and 0.75 ml 30% (w/v) BRIJ (BRIJ 35 polyoxyethylenelaurylether, 30% (w/v), Sigma Cat. No. 430AG-6) is added. The pH is adjusted to 8.6 with 4 M NaOH and the solution is diluted to 1 liter with water.

Assay with Inhibitor 1 volume unit (e.g. 80 μl) inhibitor solution is mixed with 1 volume unit (e.g. 80 μl) enzyme solution in an appropriate reaction vessel (e.g. a spectrophotometer cell or a micro titer plate) and equilibrated at 25° C. for 15 min. 1.375 volume units (e.g. 110 μl) substrate solution is added to the reaction vessel after which the absorbance at 405 nm is followed for 11 min (e.g. by measuring every $10^{th}$ or $30^{th}$ second). The slope of the absorbance curve is calculated using linear regression analysis. The slope of the absorbance curve is denoted $\alpha_{inhibitor}$.

Assay without Inhibitor 1 volume unit (e.g. 80 μl) buffer solution is mixed with 1 volume unit (e.g. 80 μl) enzyme solution in an appropriate reaction vessel (e.g. a spectrophotometer cell or a micro titer plate) and equilibrated at 25° C. for 15 min. 1.375 volume units (e.g. 110 μl) substrate solution is added to the reaction vessel after which the absorbance at 405 nm is followed for 11 min (e.g. by measuring every $10^{th}$ or $30^{th}$ second). The slope of the absorbance curve is calculated using linear regression analysis. The slope of the absorbance curve is denoted $\alpha$.

Blank 1 volume unit (e.g. 80 μl) inhibitor solution is mixed with 1 volume unit (e.g. 80 μl) buffer solution in an appropriate reaction vessel (e.g. a spectrophotometer cell or a micro titer plate) and equilibrated at 25° C. for 15 min. 1.375 volume units (e.g. 110 μl) substrate solution is added to the reaction vessel after which the absorbance at 405 nm is followed for 11 min. These measurements are not used in the calculations, but merely serve as a control that no enzyme has been added to the buffer and/or substrate solution.

Calculation of Residual Activity (RA)

The residual enzyme activity (RA) is calculated according to the below formula:

$$RA = (\alpha_{inhibitor}/\alpha) \times 100\%$$

Using the above test, the following results were obtained:

| Enzyme | Residual Activity (%) |
|---|---|
| Savinase ® | <5% |
| A98AT + Y167A + R170S + A194P | 88.0 |
| A98AI + A98G + S99H + G100S + S101A | 22.0 |
| S99SD + S99A | 27.3 |
| S99SD + S99A + A133E | 39.0 |
| S99SD + S99A + T143K | 23.0 |
| S99SD | 25.0 |
| S99SE | 27.0 |
| S99SD + S99A + S216SP | 29.2 |
| S99SD + S99A + S216SDP | 35.0 |
| S99SD + S99A + P129PD | 50.0 |
| S99SD + S99A + P129PR | 21.0 |
| S99SD + S99A + L217F + A228V + A230V | 12.0 |
| S99SD + S99A + L217LP | 97.0 |
| S99SD + S99A + L42LN | 69.2 |
| S99SR + S99T | 67.7 |
| S99SQ + S99T | 25.0 |
| S99SD + M222S | 25.0 |
| S99SD + N76D + A194P + A230V | 18.4 |
| S99SN | 19.0 |
| S99SD + S99A + P131T | 35.6 |

As it appears, the subtilase variants were inhibited to a much smaller extent than the parent subtilase, i.e. savinase®.

EXAMPLE 5

Performance of the Subtilase Variant of the Invention in Automatic Dishwashing (ADW)

The performance of the variant of the invention in ADW was tested in a commercial available household dishwash composition (Somat Turbo, from Henkel Washmittel GmbH) using standard conditions. The soil used was an egg/milk mixture coated on a steel plate. Further, a ballast soil containing various foodstuffs was added.

| | |
|---|---|
| Detergent: | Somat Turbo |
| Detergent dosage | 4.0 g/l |
| pH | 10.7 (as is) |
| Water hardness: | 3° dH (machine ion exchanger) |
| Temperature: | 55° C. |
| Enzyme concentration: | 20 nM and 40 nM, based on the total volume of wash water in the machine |
| Test method: | Egg/milk soiling on steel plates as described below |
| Machine: | Cylinda Compact |
| Wash program: | Program 4 without pre-flush |

Materials 220 ml full cream milk 15 eggs, medium size

Steel plates, diameter 18 cm

The Somat Turbo dishwash composition was heated at 85° C. for 5 minutes in a microwave oven in order to inactivate enzyme activity in the composition.

Soiling of Steel Plates 220 ml full cream milk was mixed with 15 raw eggs in a Braun UK 20 kitchen machine for 2 minutes, After sieving, stainless steel plates were soiled in the mixture by immersion.

The plates were dried overnight at room temperature in an upright position. The dried plates were then heated at 120° C. for 45 minutes in order to denature the proteins on the surface.

ADW Experiments

For each experiment, 10 soiled plates were washed without pre-wash (Program 4) in a Cylinda Compact machine. In addition to the soiled plates, the machine was filled up with 10 porcelain plates, 4 glasses, 4 cups and 16 pieces of cutlery.

Furthermore, 50 g of ballast slurry was added to the machine. The composition of the slurry was as follows:

Potato starch (5.43%), wheat flour (4.38%), vegetable oil (4.32%), margarine (4.32%), lard (4.32%), cream (8.76%), full cream milk (8.76%), eggs (8.76%), tomato ketchup (3.00%), barbecue sauce (2.19%), mustard (4.00%), benzoic acid (0.73%), water (3 mM $Ca^{2+}+Mg^{2+}$) (36.71%).

Measurements and Calculations

The light reflection values (R-values) were measured at six different locations on the plates using a Minolta Chroma Meter (Type: CR-300). Measurements were made on clean plates ($R_{clean}$), on soiled plates after heating ($R_{soiled}$) and on plates after wash ($R_{after\ wash}$).

The removed protein film (% RPF) was calculated according to the below formula:

$$\%RPF = 100\% \times (R_{after\ wash} - R_{soiled})/(R_{clean} - R_{soiled})$$

Using the above test method the following results were obtained (± indicates the standard deviation):

| Enzyme | % RPF (20 nM) | % RPF (40 nm) |
|---|---|---|
| Savinase ® | 3.9 ± 1.6 | 3.0 ± 1.0 |
| S99SD + S99A | 13.8 ± 5.2 | 77.1 ± 2.2 |

As it appears, the variant of the invention has a superior performance as compared to Savinase®.

EXAMPLE 6
Wash Performance of the Subtilase Variant of the Invention in a Commercially Available Powder Detergent In order to assess the wash performance of selected subtilase variants in a commercial detergent composition, standard washing experiments were performed using the below experimental conditions:

| | |
|---|---|
| Detergent dosage: | 4 g/l |
| Wash temperature: | 30° C. |
| Washing time: | 20 minutes |
| Water hardness: | 15° dH ($Ca^{2+}:Mg^{2+} = 4:1$) |
| pH: | Not adjusted |
| Enzyme concentrations: | 1, 2, 5, 10, 30 nM |

-continued

| | |
|---|---|
| Test system: | 150 ml glass beakers with a stirring rod |
| Textile/volume: | 5 textile pieces (Ø 2.5 cm) in 50 ml detergent |
| Test material: | WFK10N (egg stains) |

The detergent used was obtained from supermarket in Germany (Persil Megapearls). Prior to use all enzymatic activity was in the detergents were inactivated by microwave treatment (5 minutes, 85° C.).

The reflectance measurements were performed as described in Example 3 herein.

The data (the R values) were evaluated as follows:

A variant having a higher R-value than savinase® was given the value 1.
A variant having a lower R-value than savinase® was given the value −1.
A variant having a R-value similar to savinase® was given the value 0.

Results

| Variant | Value |
|---|---|
| Savinase ® | 0 |
| L96LA | 1 |
| L96LA + A98T + A108C + A138C | 1 |
| G97GI + S99T | 1 |

As I appears, the subtilase variants exhibit improved wash performance in a commercial detergent as compared to savinase®.

What is claimed is:

1. A method for removing egg stains from a hard surface or from laundry, comprising contacting the hard surface or laundry with a composition comprising a subtilase variant which comprises a modification in an amino acid sequence of a subtilase, wherein the modification is an insertion of one or more amino acid residues in the active site loop (b) region corresponding to positions 95–103, wherein the positions are numbered according to the amino acid sequence of the mature subtilisin BPN' set forth in SEQ ID NO:38.

2. The method of claim 1, wherein the insertion is between positions 95 and 96.

3. The method of claim 1, wherein the insertion is between positions 96 and 97.

4. The method of claim 1, wherein the insertion is between positions 97 and 98.

5. The method of claim 1, wherein the insertion is between positions 98 and 99.

6. The method of claim 1, wherein the insertion is between positions 99 and 100.

7. The method of claim 1, wherein the insertion is between positions 100 and 101.

8. The method of claim 1, wherein the insertion is between positions 101 and 102.

9. The method of claim 1, wherein the insertion is between positions 102 and 103.

10. The method of claim 1, wherein the insertion is between positions 103 and 104.

11. The method of claim 1, wherein the insertion is selected from the group consisting of X98XA, X98XT, X98XG and X98XS.

12. The method of claim 1, wherein the insertion is selected from the group consisting of X99XD, X99XE, X99XK and X99XR.

13. The method of claim 1, wherein the subtilase variant comprises at least one further modification at one or more other positions.

14. The method of claim 13, wherein the at least one further modification is a substitution at position 99, a substitution at position 133, a substitution at position 143, a substitution at position 167, a substitution at position 170, a substitution at position 194, an insertion at position 42, an insertion at position 129, an insertion at position 216, an insertion at position 217, or a combination thereof.

15. The method of claim 14, wherein the subtilase variant comprises:
(a) an insertion of at least one amino acid residue between positions 98 and 99 and a substitution at positions 133 and 143,
(b) an insertion of at least one amino acid residue between positions 99 and 100 and a substitution at position 99,
(c) an insertion of at least one amino acid residue between positions 98 and 99 and a substitution at positions 167, 170 and 194, (d) an insertion of at least one amino acid residue between positions 99 and 100 and an insertion of at least one amino acid residue between positions 216 and 217, (e) an insertion of at least one amino acid residue between positions 99 and 100 and an insertion of at least one amino acid residue between positions 217 and 218, (f) an insertion of at least one amino acid residue between positions 99 and 100 and an insertion of at least one amino acid residue between positions 42 and 43, and, (g) an insertion of at least one amino acid residue between positions 99 and 100 and an insertion of at least one amino acid residue between positions 129 and 130.

16. The method of claim 1, wherein the subtilase belongs to the sub-group I-S1.

17. The method of claim 16, wherein the subtilase is selected from the group consisting of subtilisin I168, subtilisin BPN', subtilisin DY, and subtilisin Carlsberg.

18. The method of claim 1, wherein the subtilase belongs to the sub-group I-S2.

19. The method of claim 18, wherein the subtilase is selected from the group consisting of subtilisin 147, subtilisin 309, subtilisin PB92, and subtilisin YaB.

20. The method of claim 19, wherein the subtilase is subtilisin 309.

21. The method of claim 20, wherein the subtilase variant is S99SD+S99A.

22. The method of claim 20, wherein the subtilase variant is S99SR+S99T.

23. The method of claim 20, wherein the subtilase variant is A98AS+A133E+T143K.

24. The method of claim 20, wherein the subtilase variant is A98AT+A167A+R170S+A194P.

25. The method of claim 20, wherein the subtilase variant is S99SD+S99A+P129PD.

26. The method of claim 20, wherein the subtilase variant is S99SD+S99A+S216SP.

27. The method of claim 20, wherein the subtilase variant is S99SD+S99A+S216SDP.

28. The method of claim 20, wherein the subtilase variant is S99SD+S99A+L217LP.

29. The method of claim 20, wherein the subtilase variant is L42LN+S99SD.

30. The method of claim 20, wherein the subtilase variant is L42LN+S99SD+S99A.

* * * * *

UNITED STATES PATENT AND TRADEMARK OFFICE
CERTIFICATE OF CORRECTION

PATENT NO.   : 6,727,085 B2
DATED        : April 27, 2004
INVENTOR(S)  : Fanø et al.

It is certified that error appears in the above-identified patent and that said Letters Patent is hereby corrected as shown below:

Column 98,
Line 23, please insert the following claims:
-- Claim 31 The method of claim 45, wherein the subtilase is subtilisin 309.
  Claim 32 The method of claim 46, wherein the subtilase is subtilisin 309.
  Claim 33 The method of claim 47, wherein the subtilase is subtilisin 309.
  Claim 34 The method of claim 48, wherein the subtilase is subtilisin 309.
  Claim 35 The method of claim 49, wherein the subtilase is subtilisin 309.
  Claim 36 The method of claim 50, wherein the subtilase is subtilisin 309.
  Claim 37 The method of claim 51, wherein the subtilase is subtilisin 309.
  Claim 38 The method of claim 52, wherein the subtilase is subtilisin 309.
  Claim 39 The method of claim 53, wherein the subtilase is subtilisin 309. --

Signed and Sealed this

Twenty-seventh Day of July, 2004

JON W. DUDAS
*Acting Director of the United States Patent and Trademark Office*

SEQUENCE LISTING

<160> NUMBER OF SEQ ID NOS: 105

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Gly Lys Ala Ser
1

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cagaagatgt ggacgcgctt g                                                   21

<210> SEQ ID NO 3
<211> LENGTH: 50

```
<212> TYPE: DNA
<213> ORGANISM: Artificial Sequence
<220> FEATURE:
<223> OTHER INFORMATION: Primer

<400> SEQUENCE: 3
ctgcacgttt accccgggtg cgacaatgtc aaggcctggg ccatactgtg            50

<210> SEQ ID NO 4
<211> LENGTH: 52
<212> TYPE: DNA
<213> ORGANISM: Artificial Sequence
<220> FEATURE:
<223> OTHER INFORMATION: Primer

<400> SEQUENCE: 4
ctcgatacag ggatatccac tcatccagat ctaaacaata ttcgtggtgg cg         52

<210> SEQ ID NO 5
<211> LENGTH: 40
<212> TYPE: DNA
<213> ORGANISM: Artificial Sequence
<220> FEATURE:
<223> OTHER INFORMATION: Primer

<400> SEQUENCE: 5
ccgaacctga accatccgcg gcccctagga ctttaacagc                        40

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
aaccgcacag cgtttttta ttgattaacg cgttgc                            36

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
tgaaccgctg gtggggccta ggactttaac ag                                32

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gattaacgcg ttgccgcttc tg                                           22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
```

-continued

```
cagaagatgt ggacgcgctt g                                              21

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gaccgaacct gaaccctgag tggcgcctag gac                                 33

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gattaacgcg ttgccgcttc tg                                             22

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
gagttaagcc cagaagatgt ggacgcg                                        27

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gaccgaacct gaaccatcgc tcgcccctag gac                                 33

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
aggagtagcc gacgatgtac cgtttaa                                        27

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
gagttaagcc cagaagatgt ggacgcg                                        27

<210> SEQ ID NO 16
<211> LENGTH: 6
<212> TYPE: PRT
<213> ORGANISM: Artificial Sequence
```

<220> FEATURE:
<223> OTHER INFORMATION: Synthetic

<400> SEQUENCE: 16

Ala Gly Lys Ala Ser Leu
1               5

<210> SEQ ID NO 17
<211> LENGTH: 70
<212> TYPE: DNA
<213> ORGANISM: Artificial Sequence
<220> FEATURE:
<223> OTHER INFORMATION: Primer

<400> SEQUENCE: 17
ccattccaat ccctggcaaa tcgagctgac cgaacctgaa ccgctggtac ccgctaggac    60
tttaacagcg                                                           70

<210> SEQ ID NO 18
<211> LENGTH: 44
<212> TYPE: DNA
<213> ORGANISM: Artificial Sequence
<220> FEATURE:
<223> OTHER INFORMATION: Primer

<400> SEQUENCE: 18
aacgcctcta gaagtcgcgc tattaacaca ttgctcgagt gtgg                     44

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
aaccgcacag cgttttttta ttgattaacg cgttgc                              36

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
cagaagatgt ggacgcgctt g                                              21

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
aaccgctggt ggcgtctagg actttaacag cg                                  32

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22

-continued gattaacgcg ttgccgcttc tg                22

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
cagaagatgt ggacgcgctt g                21

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
aaccgctggt ggcttctagg actttaacag cg                32

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
gattaacgcg ttgccgcttc tg                22

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
gagttaagcc cagaagatgt ggacgcg                27

<210> SEQ ID NO 27
<211> LENGTH: 4
<212> TYPE: PRT
<213> ORGANISM: Artificial Sequence
<220> FEATURE:
<223> OTHER INFORMATION: Synthetic

<400> SEQUENCE: 27

Ala Gly Gly Leu
1

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
accgaacctg aacctgcgct cgcccctagg                30

<210> SEQ ID NO 29
<211> LENGTH: 21

```
<212> TYPE: DNA
<213> ORGANISM: Artificial Sequence
<220> FEATURE:
<223> OTHER INFORMATION: Primer

<400> SEQUENCE: 29
cagaagatgt ggacgcgctt g                                          21

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
gaccgaacct gagccctcgg tggcgcctag gac                             33

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
gattaacgcg ttgccgcttc tg                                         22

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
cccttcgcca agtgagactc tcgagcaagc tg                              32

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
acagcgtttt tttattgatt aacgcgttgc                                 30

<210> SEQ ID NO 34
<211> LENGTH: 39
<212> TYPE: DNA
<213> ORGANISM: Artificial Sequence
<220> FEATURE:
<223> OTHER INFORMATION: Primer

<400> SEQUENCE: 34
aaagtcctag gggccgccga cggttcaggt tcggtcagc                       39

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
```
gagttaagcc cagaagatgt ggacgcg                                           27

<210> SEQ ID NO 36
<211> LENGTH: 32
<212> TYPE: DNA
<213> ORGANISM: Artificial Sequence
<220> FEATURE:
<223> OTHER INFORMATION: Primer

<400> SEQUENCE: 36
tgttaatagc gcgaaatcca gaggcgttct tg                                      32

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
acagcgtttt tttattgatt aacgcgttgc                                         30

<210> SEQ ID NO 38
<211> LENGTH: 275
<212> TYPE: PRT
<213> ORGANISM: B. amyloliquefaciens

<400> SEQUENCE: 38

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

-continued

```
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
            260                 265                 270
Ala Ala Gln
        275

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
aaagtcctag gggccgccga cggttcaggt tcggtcagc                              39

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
gagttaagcc cagaagatgt ggacgcg                                           27

<210> SEQ ID NO 41
<211> LENGTH: 27
<212> TYPE: DNA
<213> ORGANISM: Artificial Sequence
<220> FEATURE:
<223> OTHER INFORMATION: Primer

<400> SEQUENCE: 41
gagttaagcc cagaagatgt ggacgcg                                           27

<210> SEQ ID NO 42
<211> LENGTH: 40
<212> TYPE: DNA
<213> ORGANISM: Artificial Sequence
<220> FEATURE:
<223> OTHER INFORMATION: Primer

<400> SEQUENCE: 42
ccgaacctga accatccgcg gcccctagga ctttaacagc                             40

<210> SEQ ID NO 43
<211> LENGTH: 35
<212> TYPE: DNA
<213> ORGANISM: Artificial Sequence
<220> FEATURE:
<223> OTHER INFORMATION: Primer

<400> SEQUENCE: 43
gatgtaccgt ttaaagggct ggcatatgtt gaacc                                  35

<210> SEQ ID NO 44
<211> LENGTH: 36
<212> TYPE: DNA
<213> ORGANISM: Artificial Sequence
<220> FEATURE:
<223> OTHER INFORMATION: Primer

<400> SEQUENCE: 44
```

-continued

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
gagttaagcc cagaagatgt ggacgcg           27

<210> SEQ ID NO 46
<211> LENGTH: 40
<212> TYPE: DNA
<213> ORGANISM: Artificial Sequence
<220> FEATURE:
<223> OTHER INFORMATION: Primer

<400> SEQUENCE: 46
ccgaacctga accatccgcg gcccctagga ctttaacagc           40

<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47
gtaccgttta aaggatcgct ggcatatgtt gaacc           35

<210> SEQ ID NO 48
<211> LENGTH: 36
<212> TYPE: DNA
<213> ORGANISM: Artificial Sequence
<220> FEATURE:
<223> OTHER INFORMATION: Primer

<400> SEQUENCE: 48
aaccgcacag cgttttttta ttgattaacg cgttgc           36

<210> SEQ ID NO 49
<211> LENGTH: 269
<212> TYPE: PRT
<213> ORGANISM: Bacillus lentus

<400> SEQUENCE: 49

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
gagttaagcc cagaagatgt ggacgcg                                        27

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
ccgaacctga accatccgcg gcccctagga ctttaacagc                          40

<210> SEQ ID NO 52
<211> LENGTH: 35
<212> TYPE: DNA
<213> ORGANISM: Artificial Sequence
<220> FEATURE:
<223> OTHER INFORMATION: Primer

<400> SEQUENCE: 52
gtgtggcact tggcgagtca gggcttccta aactc                               35

<210> SEQ ID NO 53
<211> LENGTH: 36
<212> TYPE: DNA
<213> ORGANISM: Artificial Sequence
<220> FEATURE:
<223> OTHER INFORMATION: Primer

<400> SEQUENCE: 53
aaccgcacag cgttttttta ttgattaacg cgttgc                              36

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
gagttaagcc cagaagatgt ggacgcg                               27

<210> SEQ ID NO 55
<211> LENGTH: 40
<212> TYPE: DNA
<213> ORGANISM: Artificial Sequence
<220> FEATURE:
<223> OTHER INFORMATION: Primer

<400> SEQUENCE: 55
ccgaacctga accatccgcg gcccctagga ctttaacagc                 40

<210> SEQ ID NO 56
<211> LENGTH: 35
<212> TYPE: DNA
<213> ORGANISM: Artificial Sequence
<220> FEATURE:
<223> OTHER INFORMATION: Primer

<400> SEQUENCE: 56
gtgtggcact tggcgatcga gggcttccta aactc                      35

<210> SEQ ID NO 57
<211> LENGTH: 36
<212> TYPE: DNA
<213> ORGANISM: Artificial Sequence
<220> FEATURE:
<223> OTHER INFORMATION: Primer

<400> SEQUENCE: 57
aaccgcacag cgttttttta ttgattaacg cgttgc                     36

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
gagttaagcc cagaagatgt ggacgcg                               27

<210> SEQ ID NO 59
<211> LENGTH: 40
<212> TYPE: DNA
<213> ORGANISM: Artificial Sequence
<220> FEATURE:
<223> OTHER INFORMATION: Primer

<400> SEQUENCE: 59
ccgaacctga accatccgcg gcccctagga ctttaacagc                 40

<210> SEQ ID NO 60
<211> LENGTH: 13222
<212> TYPE: DNA
<213> ORGANISM: Artificial Sequence
<220> FEATURE:
<223> OTHER INFORMATION: Synthetic

```
<400> SEQUENCE: 60
aattccggcc caacgatggc tgatttccgg gttgacggcc ggcggaacca agggggtgatc     60
ggtcggcgga aatgaaggcc tgcggcgagt gcgggccttc ttaaggccgg gttgctaccg    120
actaaaggcc caactgccgg ccgccttggt tccccactag ccagccgcct ttacttccgg    180
acgccgctca cgcccggaag tgttttgagg attataatca gagtatattg aaagtttcgc    240
gatcttttcg tataattgtt ttaggcatag tgcaatcgat tgtttgagaa agaagaaga     300
acaaaactcc taatattagt ctcatataac tttcaaagcg ctagaaaagc atattaacaa    360
aatccgtatc acgttagcta acaaactctt ttcttcttct ccataaaaat accttgtctg    420
tcatcagaca gggtattttt tatgctgtcc agactgtccg ctgtgtaaaa ataaggaata    480
aagggggtt gttattattt ggtatttta tggaacagac agtagtctgt cccataaaaa     540
atacgacagg tctgacaggc gacacatttt tattccttat ttccccccaa caataataaa    600
tactgatatg taaaatataa tttgtataag aaaatgagag ggagaggaaa catgattcaa    660
aaacgaaagc ggacagtttc gttcagactt gtgcttatgt atgactatac atttttatatt   720
aaacatattc ttttactctc cctctccttt gtactaagtt tttgctttcg cctgtcaaag    780
caagtctgaa cacgaataca gcacgctgtt atttgtcagt ttgccgatta caaaaacatc    840
agccgtaaat ggcacgctga tgcagtattt tgaatgtat acgccgaacg acggccagca    900
cgtgcgacaa taaacagtca aacggctaat gttttgtag tcggcattta ccgtgcgact    960
acgtcataaa acttaccata tgcggcttgc tgccggtcgt ttggaaacga ttgcagaatg  1020
atgcggaaca tttatcggat taacttaacg ttaatatttg tttcccaata ggcaaatctt  1080
tctaactttg atacgtttaa aacctttgct aacgtcttac tacgccttgt aaatagccta  1140
attgaattgc aattataaac aaagggttat ccgtttagaa agattgaaac tatgcaaatt  1200
actaccagct tggacaagtt ggtataaaaa tgaggaggga aaccgaatga agaaaccgtt  1260
ggggaaaatt gtcgcaagca ccgcactact catttctgtt tgatggtcga acctgttcaa  1320
ccatatttt actcctccct ttggcttact tcttttggcaa ccccttttaa cagcgttcgt   1380
ggcgtgatga gtaaagacaa gcttttagtt catcgatcgc atcggctgct gaagaagcaa  1440
aagaaaaata tttaattggc tttaatgagc aggaagctgt cagtgagttt gtagaacaag  1500
cgaaaatcaa gtagctagcg tagccgacga cttcttcgtt ttctttttat aaattaaccg  1560
aaattactcg tccttcgaca gtcactcaaa catcttgttc tagaggcaaa tgacgaggtc  1620
gccattctct ctgaggaaga ggaagtcgaa attgaattgc ttcatgaatt tgaaacgatt  1680
cctgtttat ccgttgagtt atctccgttt actgctccag cggtaagaga gactccttct   1740
ccttcagctt taacttaacg aagtacttaa actttgctaa ggacaaaata ggcaactcaa  1800
aagcccagaa gatgtggacg cgcttgaact cgatccagcg atttcttata ttgaagagga  1860
tgcagaagta acgacaatgg cgcaatcggt accatgggga ttcgggtctt ctacacctgc  1920
gcgaacttga gctaggtcgc taaagaatat aacttctcct acgtcttcat tgctgttacc  1980
gcgttagcca tggtacccct attagccgtg tgcaagcccc agctgcccat aaccgtggat  2040
tgacaggttc tggtgtaaaa gttgctgtcc tcgatacagg gatatccact catccagatc  2100
taatcggcac acgttcgggg tcgacgggta ttggcaccta actgtccaag accacatttt  2160
caacgacagg agctatgtcc ctataggtga gtaggtctag taaatattcg tggtggcgca  2220
agctttgtac cagggggaacc gtcgactcaa gatgggaatg gcatggcac gcatgtggcc   2280
gggacgatcg ctgctttaaa atttataagc accaccgcgt tcgaaacatg gtccccttgg  2340
```

```
cagctgagtt ctacccttac ccgtaccgtg cgtacaccgg ccctgctagc gacgaaattt    2400
caattcgatt ggcgttcttg gcgtagctcc tagcgctgag ctatacgctg ttaaagtcct    2460 agggcgagc ggttcaggtt cggtcagctc gattgcccaa gttaagctaa ccgcaagaac     2520
cgcatcgagg atcgcgactc gatatgcgac aatttcagga tccccgctcg ccaagtccaa    2580
gccagtcgag ctaacgggtt ggattggaat gggcagggaa caatggcatg cacgttgcta    2640
atttgagttt aggaagccct tcgccaagtg ccacactcga gcaagctgtt aatagcgcga    2700 cctaaccta cccgtccctt gttaccgtac gtgcaacgat taaactcaaa tccttcggga    2760
agcggttcac ggtgtgagct cgttcgacaa ttatcgcgct cttctagagg cgttcttgtt    2820
gtagcggcat ctgggaattc aggtgcaggc tcaatcagct atccggcgcg ctatgcgaac    2880
gcaatggcag tcggagctac gaagatctcc gcaagaacaa catcgccgta gacccttaag    2940
tccacgtccg agttagtcga taggccgcgc gatacgcttg cgttaccgtc agcctcgatg    3000
tgatcaaaac aacaaccgcg ctagcttttc acagtatggc gcaggccttg acattgtcgc    3060
acccggggta aacgtgcaga gcacataccc aggttcaaca actagttttg ttgttggcgc    3120
gatcgaaaag tgtcataccg cgtccggaac tgtaacagcg tgggcccccat ttgcacgtct    3180 cgtgtatggg tccaagttgt tatgccagct taaacggtac atcgatggct actcctcatg    3240
ttgcaggtgc ggccgcccctt gttaaacaaa agaacccatc ttggtctaat gtacaaattc    3300
atacggtcga atttgccatg tagctaccga tgaggagtac aacgtccacg ccggcgggaa    3360
caatttgttt tcttgggtag aaccagatta catgtttaag gaaatcatct aaagaatacg    3420
gcaactagtt taggaagcac gaacttgtat ggaagcggca ttgttaacgc agaagcggca    3480
acgcgttaat caataaaaaa ctttagtaga tttcttatgc cgttgatcaa atccttcgtg    3540
cttgaacata ccttcgcctg aacaattgcg tcttcgccgt tgcgcaatta gttattttt     3600 acgctgtgcg gttaaagggc acagcgtttt tttgtgtatg gatcagcttg gcgtaatcat    3660
ggtcatagct gtttcctgtg tgaaattgtt atccgctcac tgcgacacgc caatttcccg    3720
tgtcgcaaaa aaacacatac ctagtcgaac cgcattagta ccagtatcga caaaggacac    3780
actttaacaa taggcgagtg aattccacac aacatacgag ccggaagcat aaagtgtaaa    3840
gcctggggtg cctaatgagt gagctaactc acattaattg cgttgcgctc actgcccgct    3900
ttaaggtgtg ttgtatgctc ggccttcgta tttcacattt cggaccccac ggattactca    3960
ctcgattgag tgtaattaac gcaacgcgag tgacgggcga ttccagtcgg gaaacctgtc    4020
gtgccagctg cattaatgaa tcggccaacg cgcggggaga ggcggtttgc gtattgggcg    4080
ctcttccgct tcctcgctca aggtcagcc cttttggacag cacggtcgac gtaattactt    4140
agccggttgc gcgccccctct ccgccaaacg cataacccgc gagaaggcga aggagcgagt    4200
ctgactcgct gcgctcggtc gttcggctgc ggcgagcggg atcagctcac tcaaaggcgg    4260
taatacggtt atccacagaa tcaggggata acgcaggaaa gactgagcga cgcgagccag    4320
caagccgacg ccgtcgcca tagtcgagtg agtttccgcc attatgccaa taggtgtctt    4380
agtcccctat tgcgtccttt gaacatgtga gcaaaaggcc agcaaaaggc caggaaccgt    4440
aaaaaggccg cgttgctggc gttttttccat aggctccgcc ccctgacga gcatcacaaa    4500 cttgtacact cgttttccgg tcgttttccg gtccttggca ttttccggc gcaacgaccg    4560 caaaaaggta tccgaggcgg ggggactgct cgtagtgttt aatcgacgct caagtcagag    4620
gtggcgaaac ccgacaggac tataaagata ccaggcgttt cccctggaa gctccctcgt    4680
```

```
gcgctctcct gttccgaccc ttagctgcga gttcagtctc caccgctttg ggctgtcctg   4740
atatttctat ggtccgcaaa gggggacctt cgagggagca cgcgagagga caaggctggg   4800
tgccgcttac cggatacctg tccgcctttc tcccttcggg aagcgtggcg ctttctcata   4860
gctcacgctg taggtatctc agttcggtgt aggtcgttcg acggcgaatg gcctatggac   4920
aggcggaaag agggaagccc ttcgcaccgc gaaagagtat cgagtgcgac atccatagag   4980
tcaagccaca tccagcaagc ctccaagctg ggctgtgtgc acgaacccc cgttcagccc    5040 gaccgctgcg ccttatccgg taactatcgt cttgagtcca acccggtaag acacgactta   5100
gaggttcgac ccgacacacg tgcttggggg gcaagtcggg ctggcgacgc ggaataggcc   5160
attgatagca gaactcaggt tgggccattc tgtgctgaat cgccactgg cagcagccac    5220 tggtaacagg attagcagag cgaggtatgt aggcggtgct acagagttct tgaagtggtg   5280
gcctaactac ggctacacta gcggtgacc gtcgtcggtg accattgtcc taatcgtctc    5340
gctccataca tccgccacga tgtctcaaga acttcaccac cggattgatg ccgatgtgat   5400
gaaggacagt atttggtatc tgcgctctgc tgaagccagt taccttcgga aaaagagttg   5460
gtagctcttg atccggcaaa caaaccaccg ctggtagcgg cttcctgtca taaaccatag   5520
acgcgagacg acttcggtca atggaagcct ttttctcaac catcgagaac taggccgttt   5580
gtttggtggc gaccatcgcc tggttttttt gtttgcaagc agcagattac gcgcagaaaa   5640
aaaggatctc aagaagatcc tttgatcttt tctacgggggt ctgacgctca gtggaacgaa   5700
accaaaaaaa caaacgttcg tcgtctaatg cgcgtctttt tttcctagag ttcttctagg   5760
aaactagaaa gatgccccca gactgcgagt caccttgctt aactcacgtt aagggatttt   5820
ggtcatgaga ttatcaaaaa ggatcttcac ctagatcctt taaattaaa aatgaagttt     5880 taaatcaatc taaagtatat ttgagtgcaa ttccctaaaa ccagtactct aatagttttt    5940
cctagaagtg atctaggaa aatttaattt ttacttcaaa atttagttag atttcatata    6000
atgagtaaac ttggtctgac agttaccaat gcttaatcag tgaggcacct atctcagcga   6060
tctgtctatt tcgttcatcc atagttgcct gactccccgt tactcatttg aaccagactg   6120
tcaatggtta cgaattagtc actccgtgga tagagtcgct agacagataa agcaagtagg   6180
tatcaacgga ctgaggggca cgtgtagata actacgatac gggagggctt accatctggc   6240
cccagtgctg caatgatacc gcgagaccca cgctcaccgg ctccagattt atcagcaata   6300
gcacatctat tgatgctatg ccctcccgaa tggtagaccg gggtcacgac gttactatgg   6360
cgctctgggt gcgagtggcc gaggtctaaa tagtcgttat aaccagccag ccggaagggc   6420
cgagcgcaga agtggtcctg caactttatc cgcctccatc cagtctatta attgttgccg   6480
ggaagctaga gtaagtagtt ttggtcggtc ggccttcccg gctcgcgtct tcaccaggac   6540
gttgaaatag gcggaggtag gtcagataat taacaacggc ccttcgatct cattcatcaa   6600
cgccagttaa tagtttgcgc aacgttgttg ccattgctac aggcatcgtg gtgtcacgct   6660
cgtcgtttgg tatggcttca ttcagctccg gttcccaacg gcggtcaatt atcaaacgcg   6720
ttgcaacaac ggtaacgatg tccgtagcac cacagtgcga gcagcaaacc ataccgaagt   6780
aagtcgaggc caagggttgc atcaaggcga gttacatgat cccccatgtt gtgcaaaaaa   6840
gcggttagct ccttcggtcc tccgatcgtt gtcagaagta agttggccgc agtgttatca   6900
tagttccgct caatgtacta gggggtacaa cacgttttt cgccaatcga ggaagccagg    6960
aggctagcaa cagtcttcat tcaaccggcg tcacaatagt ctcatggtta tggcagcact   7020
gcataattct cttactgtca tgccatccgt aagatgcttt tctgtgactg gtgagtactc   7080
```

-continued

```
aaccaagtca ttctgagaat gagtaccaat accgtcgtga cgtattaaga gaatgacagt    7140
acggtaggca ttctacgaaa agacactgac cactcatgag ttggttcagt aagactctta    7200
agtgtatgcg gcgaccgagt tgctcttgcc cggcgtcaat acgggataat accgcgccac    7260
atagcagaac tttaaaagtg ctcatcattg gaaaacgttc tcacatacgc cgctggctca    7320
acgagaacgg gccgcagtta tgccctatta tggcgcggtg tatcgtcttg aaattttcac    7380
gagtagtaac cttttgcaag ttcggggcga aaactctcaa ggatcttacc gctgttgaga    7440
tccagttcga tgtaacccac tcgtgcaccc aactgatctt cagcatcttt tacttttcacc   7500 aagccccgct tttgagagtt cctagaatgg cgacaactct aggtcaagct acattgggtg    7560
agcacgtggg ttgactagaa gtcgtagaaa atgaaagtgg agcgtttctg ggtgagcaaa    7620
aacaggaagg caaatgccg caaaaaggg aataagggcg acacggaaat gttgaatact     7680
catactcttc cttttttcaat tcgcaaagac ccactcgttt ttgtccttcc gttttacggc   7740
gttttttccc ttattcccgc tgtgccttta caacttatga gtatgagaag gaaaaagtta    7800
gatcctctac gccggacgca tcgtggccgg catcaccggc gccacaggtg cggttgctgg    7860
cgcctatatc gccgacatca ccgatgggga agatcgggct ctaggagatg cggcctgcgt    7920
agcaccggcc gtagtggccg cggtgtccac gccaacgacc gcggatatag cggctgtagt    7980
ggctacccct tctagcccga cgccacttcg ggctcatgag cgcttgtttc ggcgtgggta    8040
tggtggcagg cccgtggccg ggggactgtt gggcgccatc tccttgcatg ccttttagtc    8100
gcggtgaagc ccgagtactc gcgaacaaag ccgcacccat accaccgtcc gggcaccggc    8160
cccctgacaa cccgcggtag aggaacgtac ggaaaatcag cagctgattt cacttttttgc   8220 attctacaaa ctgcataact catatgtaaa tcgctccttt ttaggtggca caaatgtgag    8280
gcattttcgc tctttccggc gtcgactaaa gtgaaaaacg taagatgttt gacgtattga    8340
gtatacattt agcgaggaaa atccaccgt gtttacactc cgtaaaagcg agaaaggccg    8400
gaggctagtt acccttaagt tattggtatg actggttta agcgcaaaaa aagttgcttt    8460
ttcgtaccta ttaatgtatc gttagaaaac cgactgtaaa ctccgatcaa tgggaattca    8520
ataaccatac tgaccaaaat tcgcgttttt ttcaacgaaa aagcatggat aattacatag    8580
caatcttttg gctgacattt aagtacagtc ggcattatct catattataa aagccagtca    8640
ttaggcctat ctgacaattc ctgaatagag ttcataaaca atcctgcatg ataaccatca    8700
ttcatgtcag ccgtaataga gtataatatt ttcggtcagt aatccggata gactgttaag    8760
gacttatctc aagtatttgt taggacgtac tattggtagt caaacagaat gatgtacctg    8820
taaagatagc ggtaaatata ttgaattacc tttattaatg aattttcctg ctgtaataat    8880
gggtagaagg taattactat gtttgtctta ctacatggac atttctatcg ccatttatat    8940
aacttaatgg aaataattac ttaaaaggac gacattatta cccatcttcc attaatgata    9000
tattattgat atttaagtta aacccagtaa atgaagtcca tggaataata gaaagagaaa    9060
aagcattttc aggtataggt gttttgggaa acaatttccc ataataacta taaattcaat    9120
ttgggtcatt tacttcaggt accttattat ctttctcttt ttcgtaaaag tccatatcca    9180
caaacccctt tgttaaaggg cgaaccatta tatttctcta catcagaaag gtataaatca    9240
taaaactctt tgaagtcatt ctttacagga gtccaaatac cagagaatgt tttagataca    9300
gcttggtaat ataagagat gtagtctttc catatttagt attttgagaa acttcagtaa    9360
gaaatgtcct caggtttatg gtctcttaca aaatctatgt ccatcaaaaa ttgtataaag    9420
```

-continued

```
tggctctaac ttatcccaat aacctaactc tccgtcgcta ttgtaaccag ttctaaaagc    9480
tgtatttgag tttatcaccc ggtagttttt aacatatttc accgagattg aatagggtta    9540
ttggattgag aggcagcgat aacattggtc aagattttcg acataaactc aaatagtggg    9600
ttgtcactaa gaaaataaat gcagggtaaa atttatatcc ttcttgtttt atgtttcggt    9660
ataaaacact aatatcaatt tctgtggtta tactaaaagt aacagtgatt cttttattta    9720
cgtcccattt taaatatagg aagaacaaaa tacaaagcca tattttgtga ttatagttaa    9780
agacaccaat atgattttca cgtttgttgg ttcaaataat gattaaatat ctcttttctc    9840
ttccaattgt ctaaatcaat tttattaaag ttcatttgat atgcctccta aatttttatc    9900
gcaaacaacc aagtttatta ctaatttata gagaaaagag aaggttaaca gatttagtta    9960
aaataatttc aagtaaacta tacggaggat ttaaaaatag taaagtgaat ttaggaggct   10020
tacttgtctg ctttcttcat tagaatcaat cctttttttaa aagtcaatat tactgtaaca   10080
taaatatata ttttaaaaat atttcactta aatcctccga atgaacagac gaaagaagta   10140
atcttagtta ggaaaaaatt ttcagttata atgacattgt attatatat aaaatttta    10200 atcccacttt atccaatatt cgttccttaa tttcatgaac aatcttcatt ctttcttctc   10260
tagtcattat tattggtccc agatctggtt gaactactct tagggtgaaa taggttataa   10320
gcaaggaatt aaagtacttg ttagaagtaa gaaagaagag atcagtaata ataaccaggg   10380
tctagaccaa cttgatgaga ttaataaaat aatttttccg ttcccaattc cacattgcaa   10440
taatagaaaa tccatcttca tcggcttttt cgtcatcatc tgtatgaatc aaatcgcctt   10500
aattatttta ttaaaaaggc aagggttaag gtgtaacgtt attatctttt aggtagaagt   10560
agccgaaaaa gcagtagtag acatacttag tttagcggaa cttctgtgtc atcaaggttt   10620 aatttttttat gtatttcttt taacaaacca ccataggaga ttaacctttt acggtgtaaa   10680
ccttcctcca aatcagacaa gaagacacag tagttccaaa ttaaaaaata cataaagaaa   10740
attgtttggt ggtatcctct aattggaaaa tgccacattt ggaaggaggt ttagtctgtt   10800
acgtttcaaa ttcttttctt catcatcggt cataaaatcc gtatccttta caggatattt   10860
tgcagtttcg tcaattgccg attgtatatc cgatttatat tgcaaagttt aagaaaagaa   10920
gtagtagcca gtattttagg cataggaaat gtcctataaa acgtcaaagc agttaacggc   10980
taacatatag gctaaatata ttatttttcg gtcgaatcat ttgaactttt acatttggat   11040
catagtctaa tttcattgcc ttttttccaaa attgaatcca ttgttttttga ttcacgtagt   11100 aataaaaagc cagcttagta aacttgaaaa tgtaaaccta gtatcagatt aaagtaacgg   11160
aaaaaggttt taacttaggt aacaaaaact aagtgcatca tttctgtatt cttaaaataa   11220
gttggttcca cacataccaa tacatgcatg tgctgattat aagaattatc tttattattt   11280
attgtcactt ccgttgcacg aaagacataa gaattttatt caaccaaggt gtgtatggtt   11340
atgtacgtac acgactaata ttcttaatag aaataataaa taacagtgaa ggcaacgtgc   11400
cataaaacca acaagatttt tattaatttt tttatattgc atcattcggc gaaatccttg   11460
agccatatct gacaaactct tatttaattc ttcgccatca gtattttggt tgttctaaaa   11520
ataattaaaa aaatataacg tagtaagccg ctttaggaac tcggtataga ctgtttgaga   11580
ataaattaag aagcggtagt taaacatttt taactgttaa tgtgagaaac aaccaacgaa   11640
ctgttggctt tgtttaata acttcagcaa caaccttttg tgactgaatg ccatgtttca   11700
atttgtaaaa attgacaatt acactctttg ttggttgctt gacaaccgaa aacaaattat   11760
tgaagtcgtt gttggaaaac actgacttac ggtacaaagt ttgctctcct ccagttgcac   11820
```

```
attggacaaa gcctggattt acaaaaccac actcgataca actttctttc gcctgtttca    11880
cgattttgtt tatactctaa aacgagagga ggtcaacgtg taacctgttt cggacctaaa    11940
tgttttggtg tgagctatgt tgaaagaaag cggacaaagt gctaaaacaa atatgagatt    12000
tatttcagca caatctttta ctctttcagc cttttttaaat tcaagaatat gcagaagttc    12060
aaagtaatca acattagcga ttttcttttc tctccatggt ataaagtcgt gttagaaaat    12120
gagaaagtcg gaaaaattta agttcttata cgtcttcaag tttcattagt tgtaatcgct    12180
aaaagaaaag agaggtacca ctcacttttc cacttttgt cttgtccact aaaacccttg     12240 attttcatc tgaataaatg ctactattag gacacataat attaaagaa accccatct       12300 gagtgaaaag gtgaaaaaca gaacaggtga ttttgggaac taaaaagtag acttatttac    12360
gatgataatc ctgtgtatta taattttctt tgggggtaga atttagttat tgtttagtc     12420 acttataact ttaacagatg gggttttctct gtgcaaccaa ttttaagggt tttcaatact   12480
ttaaaacaca tacataccaa taaatcaata acaaatcag tgaatattga aattgtctac     12540
cccaaaaaga cacgttggtt aaaattccca aaagttatga aattttgtgt atgtatggtt    12600
cacttcaacg caccttttcag caactaaaat aaaaatgacg ttatttctat atgtatcaag   12660
ataagaaaga acaagttcaa aaccatcaaa aaaagacacc gtgaagttgc gtggaaagtc    12720
gttgatttta tttttactgc aataaagata tacatagttc tattctttct tgttcaagtt    12780
ttggtagttt ttttctgtgg ttttcaggtg cttttttat tttataaact cattgggtga     12840
tctcgacttc gttcttttt tacctctcgg ttatgagtta gttcaaattc gttctttta      12900 aaagtccac gaaaaaaata aaatatttga gtaacccact agagctgaag caagaaaaaa     12960
atggagagcc aatactcaat caagtttaag caagaaaaat ggttctaaat cgtgtttttc    13020
ttggaattgt gctgttttat cctttacctt gtctacaaac cccttaaaaa cgttttttaa    13080
ggcttttaag ccgtctgtac ccaagattta gcacaaaaag aaccttaaca cgacaaaata   13140
ggaaatggaa cagatgtttg gggaattttt gcaaaaattt ccgaaaattc ggcagacatg    13200
gttccttaag gcaaggaatt cc                                              13222
```

<210> SEQ ID NO 61
<211> LENGTH: 68
<212> TYPE: DNA
<213> ORGANISM: Artificial Sequence
<220> FEATURE:
<223> OTHER INFORMATION: Primer

<400> SEQUENCE: 61

```
aagggcggcc acacctacaa catgaggagt agccatcgat gtaccgttaa agctggcata    60
tgttgaac                                                              68
```

<210> SEQ ID NO 62
<211> LENGTH: 36
<212> TYPE: DNA
<213> ORGANISM: Artificial Sequence
<220> FEATURE:
<223> OTHER INFORMATION: Primer

<400> SEQUENCE: 62

```
aaccgcacag cgttttttta ttgattaacg cgttgc                               36
```

<210> SEQ ID NO 63
<211> LENGTH: 27
<212> TYPE: DNA

<210> SEQ ID NO 63
<211> LENGTH: 27
<212> TYPE: DNA
<213> ORGANISM: Artificial Sequence
<220> FEATURE:
<223> OTHER INFORMATION: Primer

<400> SEQUENCE: 63
gagttaagcc cagaagatgt ggacgcg                               27

<210> SEQ ID NO 64
<211> LENGTH: 40
<212> TYPE: DNA
<213> ORGANISM: Artificial Sequence
<220> FEATURE:
<223> OTHER INFORMATION: Primer

<400> SEQUENCE: 64
ccgaacctga accatccgcg gcccctagga ctttaacagc                 40

<210> SEQ ID NO 65
<211> LENGTH: 35
<212> TYPE: DNA
<213> ORGANISM: Artificial Sequence
<220> FEATURE:
<223> OTHER INFORMATION: Primer

<400> SEQUENCE: 65
catcgatgta ccgtttggta agctggcata tgttg                      35

<210> SEQ ID NO 66
<211> LENGTH: 36
<212> TYPE: DNA
<213> ORGANISM: Artificial Sequence
<220> FEATURE:
<223> OTHER INFORMATION: Primer

<400> SEQUENCE: 66
aaccgcacag cgttttttta ttgattaacg cgttgc                     36

<210> SEQ ID NO 67
<211> LENGTH: 45
<212> TYPE: DNA
<213> ORGANISM: Artificial Sequence
<220> FEATURE:
<223> OTHER INFORMATION: Primer

<400> SEQUENCE: 67
gctgttaaag tcctagggat cgcgactggt tcaggttcgg tcagc           45

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
gattaacgcg ttgccgcttc tg                                    22

<210> SEQ ID NO 69
<211> LENGTH: 39
<212> TYPE: DNA
<213> ORGANISM: Artificial Sequence
<220> FEATURE:
<223> OTHER INFORMATION: Primer

<400> SEQUENCE: 69
gttaaagtcc taggggcgtc gagcggttca ggttcggtc                  39

<210> SEQ ID NO 70
<211> LENGTH: 63
<212> TYPE: DNA
<213> ORGANISM: Artificial Sequence
<220> FEATURE:
<223> OTHER INFORMATION: Primer

<400> SEQUENCE: 70
aacgcctcta gatttcgcgc tattaacagc ttgctcgagt gtttcacttg gcgaagggct    60
tcc                                                                  63

<210> SEQ ID NO 71
<211> LENGTH: 40
<212> TYPE: DNA
<213> ORGANISM: Artificial Sequence
<220> FEATURE:
<223> OTHER INFORMATION: Primer

<400> SEQUENCE: 71
ccgaacctga accatccgcg gccctagga ctttaacagc                            40

<210> SEQ ID NO 72
<211> LENGTH: 42
<212> TYPE: DNA
<213> ORGANISM: Artificial Sequence
<220> FEATURE:
<223> OTHER INFORMATION: Primer

<400> SEQUENCE: 72
gctgttaaag tcctaggggc gggtagcggt tcaggttcgg tc                        42

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
gattaacgcg ttgccgcttc tg                                              22

<210> SEQ ID NO 74
<211> LENGTH: 63
<212> TYPE: DNA
<213> ORGANISM: Artificial Sequence
<220> FEATURE:
<223> OTHER INFORMATION: Primer

<400> SEQUENCE: 74
gtcctcgata cagggatatc cactcatcca gatctaaata ttaaaggtgg cgcaagcttt    60
gta                                                                  63

<210> SEQ ID NO 75
<211> LENGTH: 15
<212> TYPE: DNA
<213> ORGANISM: Artificial Sequence
<220> FEATURE:
<223> OTHER INFORMATION: Primer

<400> SEQUENCE: 75
taggacttta acagc                                                     15

<210> SEQ ID NO 76

<211> LENGTH: 63
<212> TYPE: DNA
<213> ORGANISM: Artificial Sequence
<220> FEATURE:
<223> OTHER INFORMATION: Primer

<400> SEQUENCE: 76
gctgttaaag tcctaggggc gtcgagcggt tcaggttcgg tcggtcgat tgcccaagga    60 ttg    63

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
gattaacgcg ttgccgcttc tg    22

<210> SEQ ID NO 78
<211> LENGTH: 51
<212> TYPE: DNA
<213> ORGANISM: Artificial Sequence
<220> FEATURE:
<223> OTHER INFORMATION: Primer

<400> SEQUENCE: 78
gctgttaaag tcctaggggc gtcgggcact ggcagcggtt caggttcggt c    51

<210> SEQ ID NO 79
<211> LENGTH: 22
<212> TYPE: DNA
<213> ORGANISM: Artificial Sequence
<220> FEATURE:
<223> OTHER INFORMATION: Primer

<400> SEQUENCE: 79
gattaacgcg ttgccgcttc tg    22

<210> SEQ ID NO 80
<211> LENGTH: 45
<212> TYPE: DNA
<213> ORGANISM: Artificial Sequence
<220> FEATURE:
<223> OTHER INFORMATION: Primer

<400> SEQUENCE: 80
gctgttaaag tcctaggggg cccagccggt tcaggttcgg tcagc    45

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
gattaacgcg ttgccgcttc tg    22

<210> SEQ ID NO 82
<211> LENGTH: 51
<212> TYPE: DNA
<213> ORGANISM: Artificial Sequence
<220> FEATURE:
<223> OTHER INFORMATION: Primer

<400> SEQUENCE: 82
gctgttaaag tcctaggggg catccattcg gcaggttcgg tcagctcgat t    51

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
gagttaagcc cagaagatgt ggacgcg    27

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
gattaacgcg ttgccgcttc tg    22

<210> SEQ ID NO 85
<211> LENGTH: 45
<212> TYPE: DNA
<213> ORGANISM: Artificial Sequence
<220> FEATURE:
<223> OTHER INFORMATION: Primer

<400> SEQUENCE: 85
gctgttaaag tcctaggggc ggcagacggt tcaggttcgg tcagc    45

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
gattaacgcg ttgccgcttc tg    22

<210> SEQ ID NO 87
<211> LENGTH: 63
<212> TYPE: DNA
<213> ORGANISM: Artificial Sequence
<220> FEATURE:
<223> OTHER INFORMATION: Primer

<400> SEQUENCE: 87
gctgttaaag tcctaggggc ggcagacggt tcaggttcgg tcagctcgat tgcccaagga    60
ttg    63

<210> SEQ ID NO 88
<211> LENGTH: 39
<212> TYPE: DNA
<213> ORGANISM: Artificial Sequence
<220> FEATURE:
<223> OTHER INFORMATION: Primer

<400> SEQUENCE: 88
ttgctcgagt gtggcactgg tcgaagggct tcctaaact    39

<210> SEQ ID NO 89
<211> LENGTH: 27
<212> TYPE: DNA
<213> ORGANISM: Artificial Sequence
<220> FEATURE:
<223> OTHER INFORMATION: Primer

<400> SEQUENCE: 89
gagttaagcc cagaagatgt ggacgcg                                          27

<210> SEQ ID NO 90
<211> LENGTH: 30
<212> TYPE: DNA
<213> ORGANISM: Artificial Sequence
<220> FEATURE:
<223> OTHER INFORMATION: Primer

<400> SEQUENCE: 90
aaccgctcgc ccctgctagg actttaacag                                       30

<210> SEQ ID NO 91
<211> LENGTH: 36
<212> TYPE: DNA
<213> ORGANISM: Artificial Sequence
<220> FEATURE:
<223> OTHER INFORMATION: Primer

<400> SEQUENCE: 91
aaccgcacag cgttttttta ttgattaacg cgttgc                                36

<210> SEQ ID NO 92
<211> LENGTH: 27
<212> TYPE: DNA
<213> ORGANISM: Artificial Sequence
<220> FEATURE:
<223> OTHER INFORMATION: Primer

<400> SEQUENCE: 92
gagttaagcc cagaagatgt ggacgcg                                          27

<210> SEQ ID NO 93
<211> LENGTH: 33
<212> TYPE: DNA
<213> ORGANISM: Artificial Sequence
<220> FEATURE:
<223> OTHER INFORMATION: Primer

<400> SEQUENCE: 93
gaccgaacct gaaccgttgc tcgcccctag gac                                   33

<210> SEQ ID NO 94
<211> LENGTH: 35
<212> TYPE: DNA
<213> ORGANISM: Artificial Sequence
<220> FEATURE:
<223> OTHER INFORMATION: Primer

<400> SEQUENCE: 94
catcgatgta ccgtttggta agctggcata tgttg                                 35

<210> SEQ ID NO 95
<211> LENGTH: 36
<212> TYPE: DNA
<213> ORGANISM: Artificial Sequence
<220> FEATURE:
<223> OTHER INFORMATION: Primer

<400> SEQUENCE: 95
aaccgcacag cgttttttta ttgattaacg cgttgc                                    36

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
gagttaagcc cagaagatgt ggacgcg                                              27

<210> SEQ ID NO 97
<211> LENGTH: 33
<212> TYPE: DNA
<213> ORGANISM: Artificial Sequence
<220> FEATURE:
<223> OTHER INFORMATION: Primer

<400> SEQUENCE: 97
gaccgaacct gaaccatcgc tcgcccctag gac                                       33

<210> SEQ ID NO 98
<211> LENGTH: 36
<212> TYPE: DNA
<213> ORGANISM: Artificial Sequence
<220> FEATURE:
<223> OTHER INFORMATION: Primer

<400> SEQUENCE: 98
aaccgcacag cgttttttta ttgattaacg cgttgc                                    36

<210> SEQ ID NO 99
<211> LENGTH: 27
<212> TYPE: DNA
<213> ORGANISM: Artificial Sequence
<220> FEATURE:
<223> OTHER INFORMATION: Primer

<400> SEQUENCE: 99
gagttaagcc cagaagatgt ggacgcg                                              27

<210> SEQ ID NO 100
<211> LENGTH: 33
<212> TYPE: DNA
<213> ORGANISM: Artificial Sequence
<220> FEATURE:
<223> OTHER INFORMATION: Primer

<400> SEQUENCE: 100
gaccgaacct gaaccttcgc tcgcccctag gac                                       33

<210> SEQ ID NO 101
<211> LENGTH: 36
<212> TYPE: DNA
<213> ORGANISM: Artificial Sequence
<220> FEATURE:
<223> OTHER INFORMATION: Primer

<400> SEQUENCE: 101
aaccgcacag cgttttttta ttgattaacg cgttgc                                    36

<210> SEQ ID NO 102

```
<211> LENGTH: 27
<212> TYPE: DNA
<213> ORGANISM: Artificial Sequence
<220> FEATURE:
<223> OTHER INFORMATION: Primer

<400> SEQUENCE: 102
gagttaagcc cagaagatgt ggacgcg                                          27

<210> SEQ ID NO 103
<211> LENGTH: 29
<212> TYPE: DNA
<213> ORGANISM: Artificial Sequence
<220> FEATURE:
<223> OTHER INFORMATION: Primer

<400> SEQUENCE: 103
tgtgtaaagt aactcatttg gtgagccag                                        29

<210> SEQ ID NO 104
<211> LENGTH: 52
<212> TYPE: DNA
<213> ORGANISM: Artificial Sequence
<220> FEATURE:
<223> OTHER INFORMATION: Primer

<400> SEQUENCE: 104
ccgactgcca ttgcgttcgc atacgacgcc ggggcgctga ttgagcctgc ac              52

<210> SEQ ID NO 105
<211> LENGTH: 36
<212> TYPE: DNA
<213> ORGANISM: Artificial Sequence
<220> FEATURE:
<223> OTHER INFORMATION: Primer

<400> SEQUENCE: 105
aaccgcacag cgttttttta ttgattaacg cgttgc                                36
```